US011266500B2

(12) United States Patent
Dehdashtian et al.

(10) Patent No.: US 11,266,500 B2
(45) Date of Patent: Mar. 8, 2022

(54) TRANSAPICAL HEART VALVE DELIVERY SYSTEM

(71) Applicant: Edwards Lifesciences Corporation, Irvine, CA (US)

(72) Inventors: Mark M. Dehdashtian, Irvine, CA (US); Jane M. Olin, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 47 days.

(21) Appl. No.: 16/438,345

(22) Filed: Jun. 11, 2019

(65) Prior Publication Data
US 2019/0290425 A1 Sep. 26, 2019

Related U.S. Application Data

(63) Continuation of application No. 15/596,409, filed on May 16, 2017, now Pat. No. 10,314,702, which is a continuation of application No. 14/316,390, filed on Jun. 26, 2014, now Pat. No. 9,662,207, which is a continuation of application No. 11/280,063, filed on Nov. 16, 2005, now Pat. No. 8,764,820.

(51) Int. Cl.
*A61F 2/24* (2006.01)
*A61F 2/958* (2013.01)

(52) U.S. Cl.
CPC .......... *A61F 2/2427* (2013.01); *A61F 2/2433* (2013.01); *A61F 2/2436* (2013.01); *A61F 2/2412* (2013.01); *A61F 2002/9583* (2013.01); *A61F 2220/0016* (2013.01)

(58) Field of Classification Search
CPC ..... A61F 2/2433; A61F 2/2436; A61F 2/2427
USPC ................................................ 623/2.11–2.19
See application file for complete search history.

(56) References Cited

U.S. PATENT DOCUMENTS

| 4,378,224 A | 3/1983 | Nimni et al. |
| 4,553,974 A | 11/1985 | Dewanjee |

(Continued)

FOREIGN PATENT DOCUMENTS

| DE | 19907646 A1 | 8/2000 |
| DE | 202010000329 U1 | 5/2010 |

(Continued)

OTHER PUBLICATIONS

Boudjemline et al., "Steps Toward Percutaneous Aortic Valve Replacement", Circulation 2002; 105: 775-778.

(Continued)

*Primary Examiner* — Suzette J Gherbi
(74) *Attorney, Agent, or Firm* — Guy L. Cumberbatch; Joel B. German

(57) ABSTRACT

A method of delivering a prosthetic heart valve to the aortic valve annulus while a patient's heart is beating is disclosed. The method includes accessing the left ventricle through an intercostal incision and forming a puncture in the left ventricle. A guidewire is advanced into the left ventricle and through the native aortic valve. An introducer is passed over the guidewire and into the left ventricle. A valve delivery device is advanced over the guidewire and through the introducer until a prosthetic heart valve positioned thereon is located within the native aortic valve. The prosthetic heart valve is then radially expanded within the aortic valve annulus for replacing the function of the native aortic valve.

21 Claims, 13 Drawing Sheets

(56) References Cited

U.S. PATENT DOCUMENTS

| | | | |
|---|---|---|---|
| 4,573,470 A | 3/1986 | Samson et al. | |
| 4,582,181 A | 4/1986 | Samson | |
| 4,605,002 A | 8/1986 | Rebuffat | |
| 4,647,283 A | 3/1987 | Carpentier et al. | |
| 4,648,881 A | 3/1987 | Carpentier et al. | |
| 4,753,652 A | 6/1988 | Langer et al. | |
| 4,944,740 A | 7/1990 | Buchbinder et al. | |
| 4,976,689 A * | 12/1990 | Buchbinder | A61M 25/09025 |
| | | | 128/898 |
| 5,059,186 A | 10/1991 | Yamamoto et al. | |
| 5,125,895 A | 6/1992 | Buchbinder et al. | |
| 5,188,636 A | 2/1993 | Fedotov | |
| 5,304,184 A | 4/1994 | Hathaway et al. | |
| 5,306,234 A | 4/1994 | Johnson | |
| 5,318,587 A | 6/1994 | Davey | |
| 5,320,632 A | 6/1994 | Heidmueller | |
| 5,350,361 A | 9/1994 | Tsukashima et al. | |
| 5,364,408 A | 11/1994 | Gordon | |
| 5,368,601 A | 11/1994 | Sauer et al. | |
| 5,370,685 A | 12/1994 | Stevens | |
| 5,374,275 A | 12/1994 | Bradley et al. | |
| 5,403,329 A | 4/1995 | Hinchcliffe | |
| 5,417,699 A | 5/1995 | Klein et al. | |
| 5,417,700 A | 5/1995 | Egan | |
| 5,425,737 A | 6/1995 | Burbank et al. | |
| 5,431,666 A | 7/1995 | Sauer et al. | |
| 5,458,572 A | 10/1995 | Campbell et al. | |
| 5,527,322 A | 6/1996 | Klein et al. | |
| 5,537,322 A | 7/1996 | Denz et al. | |
| 5,545,214 A | 8/1996 | Stevens | |
| 5,571,215 A | 11/1996 | Sterman et al. | |
| 5,707,354 A * | 1/1998 | Salmon | A61F 2/958 |
| | | | 600/585 |
| 5,713,951 A | 2/1998 | Garrison et al. | |
| 5,718,725 A | 2/1998 | Sterman et al. | |
| 5,792,152 A | 8/1998 | Klein et al. | |
| 5,792,172 A | 8/1998 | Fischell et al. | |
| 5,797,960 A | 8/1998 | Stevens et al. | |
| 5,810,850 A | 9/1998 | Hathaway et al. | |
| 5,820,631 A | 10/1998 | Nobles | |
| 5,860,990 A | 1/1999 | Nobles et al. | |
| 5,891,159 A | 4/1999 | Sherman et al. | |
| 5,924,424 A | 7/1999 | Stevens et al. | |
| 5,968,068 A | 10/1999 | Dehdashtian et al. | |
| 5,972,005 A | 10/1999 | Stalker et al. | |
| 5,972,030 A | 10/1999 | Garrison et al. | |
| 6,001,056 A | 12/1999 | Jassawalla et al. | |
| 6,013,092 A | 1/2000 | Dehdashtian et al. | |
| 6,033,378 A | 3/2000 | Lundquist et al. | |
| 6,071,273 A | 6/2000 | Euteneuer et al. | |
| 6,083,257 A | 7/2000 | Taylor et al. | |
| 6,106,540 A | 8/2000 | White et al. | |
| 6,117,144 A | 9/2000 | Nobles et al. | |
| 6,143,004 A | 11/2000 | Davis et al. | |
| 6,146,325 A | 11/2000 | Lewis et al. | |
| 6,206,893 B1 | 3/2001 | Klein et al. | |
| 6,231,563 B1 | 5/2001 | White et al. | |
| 6,245,079 B1 | 6/2001 | Nobles et al. | |
| 6,251,092 B1 | 6/2001 | Qin et al. | |
| 6,269,819 B1 | 8/2001 | Oz et al. | |
| 6,309,379 B1 * | 10/2001 | Willard | A61M 25/0026 |
| | | | 600/467 |
| 6,346,074 B1 | 2/2002 | Roth | |
| 6,358,258 B1 | 3/2002 | Arcia et al. | |
| 6,379,372 B1 | 4/2002 | Dehdashtian et al. | |
| 6,425,916 B1 | 7/2002 | Garrison et al. | |
| 6,454,777 B1 | 9/2002 | Green | |
| 6,506,339 B1 | 1/2003 | Girardot et al. | |
| 6,517,553 B2 | 2/2003 | Klein et al. | |
| 6,540,782 B1 | 4/2003 | Snyders | |
| 6,551,331 B2 | 4/2003 | Nobles et al. | |
| 6,558,418 B2 | 5/2003 | Carpentier et al. | |
| 6,562,052 B2 | 5/2003 | Nobles et al. | |
| 6,591,472 B1 | 7/2003 | Noone et al. | |
| 6,626,917 B1 | 9/2003 | Craig | |
| 6,679,268 B2 | 1/2004 | Stevens et al. | |
| 6,682,558 B2 | 1/2004 | Tu et al. | |
| 6,702,255 B2 | 3/2004 | Dehdashtian | |
| 6,716,207 B2 | 4/2004 | Farnholtz | |
| 6,726,717 B2 | 4/2004 | Alfieri et al. | |
| 6,730,118 B2 | 5/2004 | Spenser et al. | |
| 6,733,509 B2 | 5/2004 | Nobles et al. | |
| 6,743,239 B1 | 6/2004 | Kuehn et al. | |
| 6,746,471 B2 | 6/2004 | Mortier et al. | |
| 6,749,630 B2 | 6/2004 | McCarthy et al. | |
| 6,800,065 B2 * | 10/2004 | Duane | A61M 25/09041 |
| | | | 604/96.01 |
| 6,805,710 B2 | 10/2004 | Bolling et al. | |
| 6,821,297 B2 | 11/2004 | Snyders | |
| 6,830,584 B1 | 12/2004 | Seguin | |
| 6,837,898 B2 * | 1/2005 | Boyle | A61F 2/013 |
| | | | 606/200 |
| 6,858,039 B2 | 2/2005 | McCarthy | |
| 6,890,330 B2 | 5/2005 | Streeter et al. | |
| 6,893,460 B2 | 5/2005 | Spenser et al. | |
| 6,899,704 B2 | 5/2005 | Sterman et al. | |
| 6,908,481 B2 | 6/2005 | Cribier | |
| 6,911,034 B2 | 6/2005 | Nobles et al. | |
| 6,978,176 B2 | 12/2005 | Lattouf | |
| 6,994,666 B2 | 2/2006 | Shannon et al. | |
| 7,004,952 B2 | 2/2006 | Nobles et al. | |
| 7,078,163 B2 | 7/2006 | Torrianni | |
| 7,090,686 B2 | 8/2006 | Nobles et al. | |
| 7,100,614 B2 | 9/2006 | Stevens et al. | |
| 7,160,322 B2 | 1/2007 | Gabbay | |
| 7,201,772 B2 | 4/2007 | Schwammenthal et al. | |
| 7,252,682 B2 | 8/2007 | Seguin | |
| 7,261,732 B2 | 8/2007 | Justino | |
| 7,273,468 B2 | 9/2007 | Bedell | |
| 7,276,078 B2 | 10/2007 | Spenser et al. | |
| 7,294,148 B2 | 11/2007 | McCarthy | |
| 7,323,004 B2 | 1/2008 | Parihar | |
| 7,373,207 B2 | 5/2008 | Lattouf | |
| 7,377,926 B2 | 5/2008 | Topper et al. | |
| 7,399,315 B2 | 7/2008 | Iobbi | |
| 7,470,285 B2 | 12/2008 | Nugent et al. | |
| 7,510,572 B2 | 3/2009 | Gabbay | |
| 7,510,574 B2 | 3/2009 | L et al. | |
| 7,513,908 B2 | 4/2009 | Lattouf | |
| 7,534,260 B2 | 5/2009 | Lattouf | |
| 7,569,062 B1 | 8/2009 | Kuehn et al. | |
| 7,578,843 B2 | 8/2009 | Shu | |
| 7,604,650 B2 | 10/2009 | Bergheim | |
| 7,611,535 B2 | 11/2009 | Woolfson et al. | |
| 7,648,528 B2 | 1/2010 | Styrc | |
| 7,674,252 B2 * | 3/2010 | DeVaux | A61F 2/01 |
| | | | 604/526 |
| 7,717,955 B2 | 5/2010 | Lane et al. | |
| 7,780,723 B2 | 8/2010 | Taylor | |
| 7,803,167 B2 | 9/2010 | Nobles et al. | |
| 7,803,185 B2 | 9/2010 | Gabbay | |
| 7,806,927 B2 | 10/2010 | Styrc | |
| 7,905,892 B2 | 3/2011 | Nobles et al. | |
| 8,025,695 B2 | 9/2011 | Fogarty et al. | |
| 8,075,606 B2 | 12/2011 | Dorn | |
| 8,182,530 B2 | 5/2012 | Huber | |
| 8,475,522 B2 * | 7/2013 | Jimenez | A61F 2/2418 |
| | | | 623/2.11 |
| 8,721,713 B2 | 5/2014 | Tower et al. | |
| 8,764,820 B2 * | 7/2014 | Dehdashtian | A61F 2/24 |
| | | | 623/2.11 |
| 8,945,208 B2 * | 2/2015 | Jimenez | A61F 2/2418 |
| | | | 623/2.11 |
| 9,480,556 B2 | 11/2016 | Revuelta et al. | |
| 9,662,207 B2 * | 5/2017 | Dehdashtian | A61F 2/2433 |
| 9,717,594 B2 * | 8/2017 | Jimenez | A61M 25/0136 |
| 10,149,757 B2 * | 12/2018 | Dehdashtian | A61F 2/2433 |
| 10,314,702 B2 * | 6/2019 | Dehdashtian | A61F 2/2427 |
| 10,500,044 B2 * | 12/2019 | Jimenez | A61F 2/2427 |
| 2001/0001812 A1 | 5/2001 | Valley et al. | |
| 2001/0025643 A1 | 10/2001 | Foley | |
| 2002/0032481 A1 | 3/2002 | Gabbay | |
| 2002/0123802 A1 | 9/2002 | Snyders | |
| 2002/0128707 A1 | 9/2002 | Kavteladze et al. | |

(56) References Cited

U.S. PATENT DOCUMENTS

| | | |
|---|---|---|
| 2002/0151970 A1 | 10/2002 | Garrison et al. |
| 2002/0165571 A1 | 11/2002 | Hebert et al. |
| 2002/0183839 A1 | 12/2002 | Garrison et al. |
| 2003/0040792 A1 | 2/2003 | Gabbay |
| 2003/0109924 A1 | 6/2003 | Cribier |
| 2003/0114913 A1 | 6/2003 | Spenser et al. |
| 2003/0130571 A1 | 7/2003 | Lattouf |
| 2003/0163194 A1 | 8/2003 | Quijano et al. |
| 2003/0199975 A1 | 10/2003 | Gabbay |
| 2004/0034411 A1 | 2/2004 | Quijano et al. |
| 2004/0039436 A1 | 2/2004 | Spenser et al. |
| 2004/0116897 A1 | 6/2004 | Aboul-Hosn |
| 2004/0162608 A1 | 8/2004 | Haverich |
| 2004/0215139 A1 | 10/2004 | Cohen |
| 2004/0260309 A1 | 12/2004 | Packard |
| 2005/0043791 A1 | 2/2005 | McCarthy et al. |
| 2005/0049698 A1 | 3/2005 | Bolling et al. |
| 2005/0070844 A1 | 3/2005 | Chow et al. |
| 2005/0075729 A1 | 4/2005 | Nguyen et al. |
| 2005/0131533 A1 | 6/2005 | Alfieri et al. |
| 2005/0137695 A1* | 6/2005 | Salahieh ............... A61F 2/2439 623/2.11 |
| 2005/0148997 A1 | 7/2005 | Valley et al. |
| 2005/0209671 A1 | 9/2005 | Ton et al. |
| 2005/0228407 A1 | 10/2005 | Nobles et al. |
| 2005/0240200 A1 | 10/2005 | Bergheim |
| 2005/0251251 A1* | 11/2005 | Cribier ............... A61F 2/2409 623/2.11 |
| 2005/0271844 A1 | 12/2005 | Mapes et al. |
| 2006/0004439 A1 | 1/2006 | Spenser et al. |
| 2006/0036265 A1 | 2/2006 | Dant |
| 2006/0036313 A1 | 2/2006 | Vassiliades |
| 2006/0074484 A1 | 4/2006 | Huber |
| 2006/0135962 A1* | 6/2006 | Kick ............... A61M 25/09 606/108 |
| 2006/0142848 A1 | 6/2006 | Gabbay |
| 2006/0178675 A1 | 8/2006 | Hamman |
| 2006/0195120 A1 | 8/2006 | Nobles et al. |
| 2006/0212056 A1 | 9/2006 | Salvadori et al. |
| 2006/0217803 A1 | 9/2006 | Ingle et al. |
| 2006/0271064 A1 | 11/2006 | Agnew |
| 2006/0276889 A1 | 12/2006 | Chambers et al. |
| 2006/0282041 A1* | 12/2006 | Melsheimer ............... A61F 2/95 604/164.1 |
| 2006/0282102 A1 | 12/2006 | Nobles et al. |
| 2006/0293745 A1 | 12/2006 | Carpentier et al. |
| 2007/0005131 A1 | 1/2007 | Taylor |
| 2007/0010829 A1 | 1/2007 | Nobles et al. |
| 2007/0010876 A1* | 1/2007 | Salahieh ............... A61F 2/2439 623/2.11 |
| 2007/0021648 A1* | 1/2007 | Lenker ............... A61M 25/0097 600/29 |
| 2007/0021828 A1 | 1/2007 | Krolik et al. |
| 2007/0043385 A1 | 2/2007 | Nobles et al. |
| 2007/0112422 A1 | 5/2007 | Dehdashtian |
| 2007/0123979 A1 | 5/2007 | Perier et al. |
| 2007/0149987 A1 | 6/2007 | Wellman et al. |
| 2007/0203479 A1 | 8/2007 | Auth et al. |
| 2007/0203506 A1 | 8/2007 | Sibbitt et al. |
| 2007/0208550 A1 | 9/2007 | Cao et al. |
| 2007/0244552 A1* | 10/2007 | Salahieh ............... A61F 2/2418 623/2.11 |
| 2007/0250150 A1* | 10/2007 | Pal ............... A61M 25/0097 604/538 |
| 2007/0265697 A1* | 11/2007 | Goicoechea ............... A61F 2/90 623/1.15 |
| 2007/0276413 A1 | 11/2007 | Nobles |
| 2007/0276414 A1 | 11/2007 | Nobles |
| 2008/0004597 A1 | 1/2008 | Lattouf et al. |
| 2008/0033459 A1 | 2/2008 | Shafi et al. |
| 2008/0058839 A1 | 3/2008 | Nobles et al. |
| 2008/0071362 A1 | 3/2008 | Tuval et al. |
| 2008/0188873 A1 | 8/2008 | Speziali |
| 2008/0269786 A1 | 10/2008 | Nobles et al. |
| 2009/0099578 A1 | 4/2009 | Heneveld et al. |
| 2009/0240264 A1 | 9/2009 | Tuval et al. |
| 2009/0287182 A1 | 11/2009 | Bishop et al. |
| 2009/0287183 A1 | 11/2009 | Bishop et al. |
| 2010/0030242 A1 | 2/2010 | Nobles et al. |
| 2012/0016471 A1* | 1/2012 | Salahieh ............... A61F 2/2418 623/2.11 |
| 2014/0114406 A1* | 4/2014 | Salahieh ............... A61F 2/2418 623/2.11 |

FOREIGN PATENT DOCUMENTS

| | | |
|---|---|---|
| EP | 0815805 A2 | 1/1998 |
| EP | 1356793 A2 | 10/2003 |
| EP | 1447111 A1 | 8/2004 |
| EP | 0941698 B1 | 5/2005 |
| EP | 1570790 A3 | 12/2005 |
| GB | 2335146 A | 9/1999 |
| WO | 20199413211 A1 | 6/1994 |
| WO | 95/03742 A1 | 2/1995 |
| WO | 20199513021 A1 | 5/1995 |
| WO | 96/40347 A1 | 12/1996 |
| WO | 9640347 A1 | 12/1996 |
| WO | 20199903904 A1 | 1/1999 |
| WO | 0108050 A1 | 2/2001 |
| WO | 0126724 A2 | 4/2001 |
| WO | 2004019825 A1 | 3/2004 |
| WO | 2005034801 A2 | 4/2005 |
| WO | 2005107650 A2 | 11/2005 |
| WO | 2006019798 A1 | 2/2006 |
| WO | 2006023676 A1 | 3/2006 |
| WO | 2006041505 A1 | 4/2006 |
| WO | 2006127765 A1 | 11/2006 |
| WO | 2006138173 A2 | 12/2006 |
| WO | 2007002920 A2 | 1/2007 |
| WO | 2005102015 A3 | 4/2007 |
| WO | 2008058519 A1 | 5/2008 |
| WO | 2008081256 A1 | 7/2008 |
| WO | 2008088835 A1 | 7/2008 |
| WO | 2011017150 A2 | 2/2011 |

OTHER PUBLICATIONS

Brodsky, "Percutaneous Approaches to Aortic Valve Replacement", Cardiac Interventions, Dec. 2004, pp. 4-9.

Cooley, "Presidential Address: How Long Will the Heart Still Beat?", Cardiovascular Surgical Society, Texas Heart Institute, vol. 32, No. 2, 2005, pp. 126-129.

Cribier et al., "Percutaneous Transcatheter Implantation of an Aortic Valve Prosthesis for Calcific Aortic Stenosis: First Human Case Description," Circulation, vol. 106, pp. 3006-3008 (2002).

Dewey et al., "Feasibility of a Trans-Apical Approach for an Aortic Valve Implantation Using a Device Delivered Valve", Abstract Presentation at ISMICS 8th Annual Meeting, Jun. 1-4, 2005 New York.

Ferrari, M., et al., "Transarterial Aortic Valve Replacement With a Self-Expanding Stent in Pigs" Heart 2004 90: 1326-1331.

Greer et al., "Skeletal Muscle Ventricles, Left Ventricular Apex-to-Aorta Configuration: 1-11 Weeks in Circulation", Circulation 95(2): 497-502.

Gundry, "Aortic Valve Replacement by Mini-Sternotomy," Operative Techniques in Cardiac & Thoracic Surgery, vol. 3, No. 1 (February), pp. 47-53 (1998).

Huber et al., "Do Valved Stents Compromise Coronary Flow?" European Journal of Cardiothoracic Surgery, vol. 25, pp. 754-759 (2004).

Huber et al., "Ultrasound Navigation Through the Heart for Off-Pump Aortic Valved Stent Implantation: New Tools for New Goals", J. Endovasc. Ther., vol. 11, pp. 503-510 (2004).

Huber et al., "Direct Access Valve Replacement a Novel Approach for Off-Pump Valve Implantation Using Valved Stents", JACC, vol. 46, No. 2, 2005, pp. 366-370, www.content.onlinejacc.org.

Huber et al., "Transcatheter Valve Therapies", Chapter 6, Access to the Aortic Valves, pp. 80-100 (2010).

(56) References Cited

OTHER PUBLICATIONS

Jamieson et al., "Antegrade Placement of the Aortic Valve Stent: Transventricular Delivery with the ENTRATA System", EuroIntervention, pp. A14-A18 (2006).

LEIPIG Flyer, "Pioneering Techniques in Cardiac Surgery, The Fourth Series", Heart Center Leipzig Auditorium, Leipzig, Germany, Dec. 1-2, 2005.

Lichtenstein et al., "Transapical Transcatheter Aoritc Valve Implantation in Humans: Initial Clinical Experience", Circulation, 2006; 114; 591-596.

Lutter et al., "Percutaneous Valve Replacement: Current State and Future Prospects", The Annals of Thoracic Surgery, Anne Thorac Surg 2004; 78: 2199-2206.

Ma et al., "Double-Crowned Valved Stents for Off-Pump Mitral Valve Replacement", European Journal of Cardio-Thoracic Surgery 28 (2005) pp. 194-199.

Morgan et al., "Left Heart Catheterizarion by Direct Ventricular Puncture: Withstanding the Test of Time", Catheterization and Cardiovascular Diagnosis, vol. 16, pp. 87-90 (1989).

Sarnoff et al., "The Surgical Relief of Aortic Stenosis by Means of Apical—Aortic Valvular Anastomosis", Circulation, vol. 11, pp. 564-575 (1955).

Semple et al., "Left Heart Catheterization by Direct Ventricular Puncture", Brit. Heart J., 1968, 30, pp. 402-406 (1968).

Shanebrook et al., "Hemodynamics of Left Ventricular Apex-Aortic Valved Conduits", Cardiovascular Diseases, Bulletin of the Texas Heart Institute, vol. 6, No. 4, Dec. 1979.

Turgut et al., "Left Ventricular Apical Puncture: A Procedure Surviving Well Into the New Millennium", Catheterization and Cardiovascular Interventions 9: 68-73 (2000).

Vahanian et al., "Percutaneous Approaches to Valvular Disease", Circulation, vol. 109, pp. 1572-1579 (2004).

Thomas A. Vassiliades, Jr., "Off-Pump Apicoaortic Conduit Insertion for High-Risk Patients with Aortic Stenosis", European Journal of Cardio-Thoracic Surgery, 2003; 23: pp. 156-158 (2003).

Kevin P. Walsh, "Interventional Cardiology", Current Paediatrics 14, pp. 45-50 (2004).

Walther et al., "Minimally Invasive Transapical Beating Heart Aortic Valve Implantation-Proof of Concept", European Journal of Cardio-Thoracic Surgery, 31, pp. 9-15 (2007).

Webb et al., "Percutaneous Stent-Mounted Valve for Treatment of Aortic or Pulmonary Valve Disease", Vavular Heart Disease, Basic Science Review, Catheterization and Cardiovascular Interventions 63: pp. 89-93 (2004).

Webb et al., "Transcatheter Percutaneous and Transapical Aortic Valve Replacement", Thoracic and Cardiovascular Surgery, Semin Thorac Cardiovasc Surg 19: pp. 304-310 (2007).

F.L. Wellens, "Presidential Address: How Long Will the Heart Still Beat?", Denton A. Cooley Cardiovascular Surgical Society, vol. 32, No. 2, pp. 126-129 (2005).

Ye et al., "Six-Month Outcome of Transapical Transcatheter Aortic Valve Implantation in the Initial Seven Patients", European Journal of Cardio-Thoracic Surgery 31, Divisions of Cardiac Surgery and Cardiology, St. Paul's Hospital, University of British Columbia, Vancouver, Canada, pp. 16-21 (2007).

Ye et al., "Transapical Transcatheter Aortic Valve Implantation: Follow-Up to 3 Years", The Journal of Thoracic and Cardiovascular Surgery, 139, pp. 1107-1113 (2010).

Zhou et al., "Self-Expandable Valved Stent of Large Size: Off-Bypass Implantation in Pulmonary Position", European Journal of Cardio-Thoracic Surgery 24, pp. 212-216 (2003).

* cited by examiner

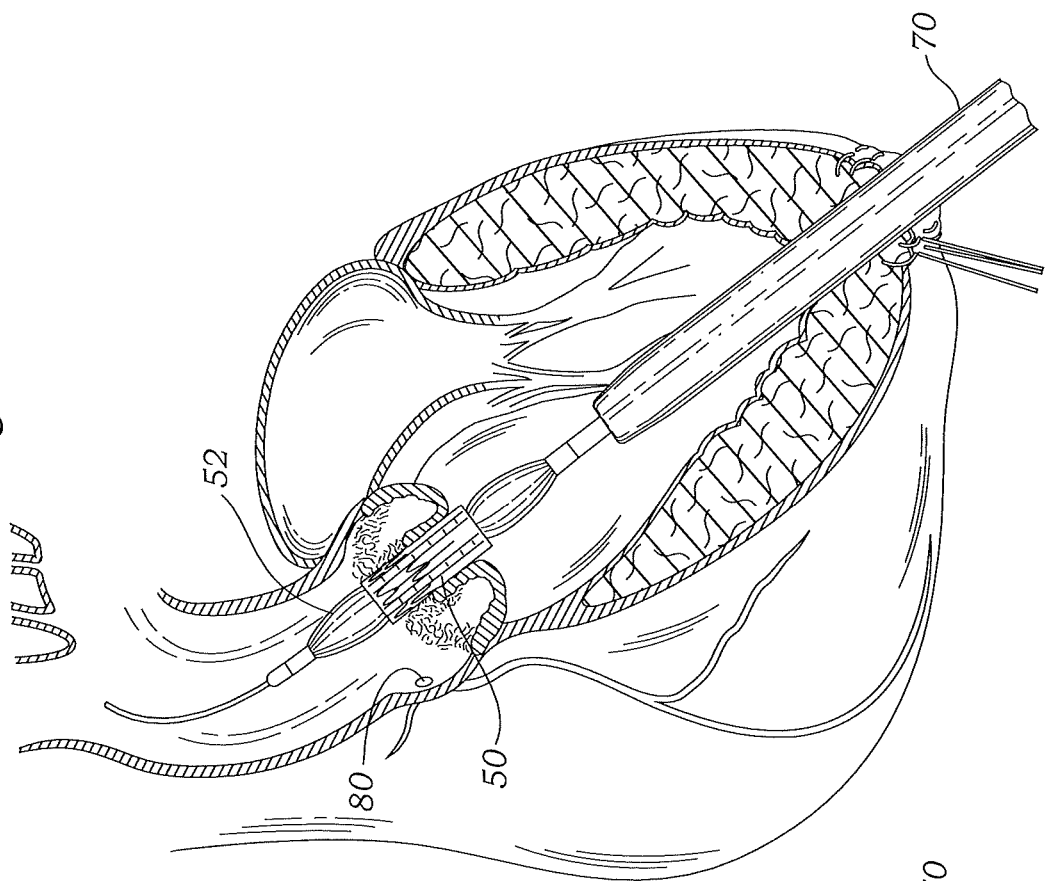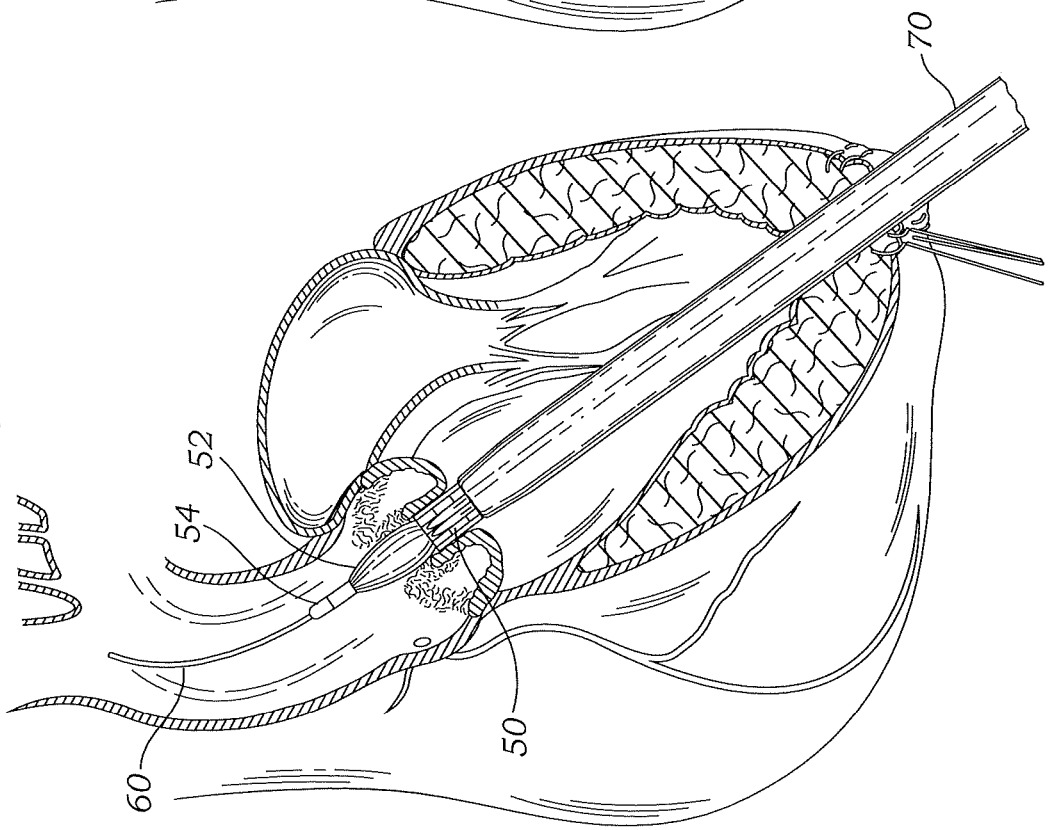

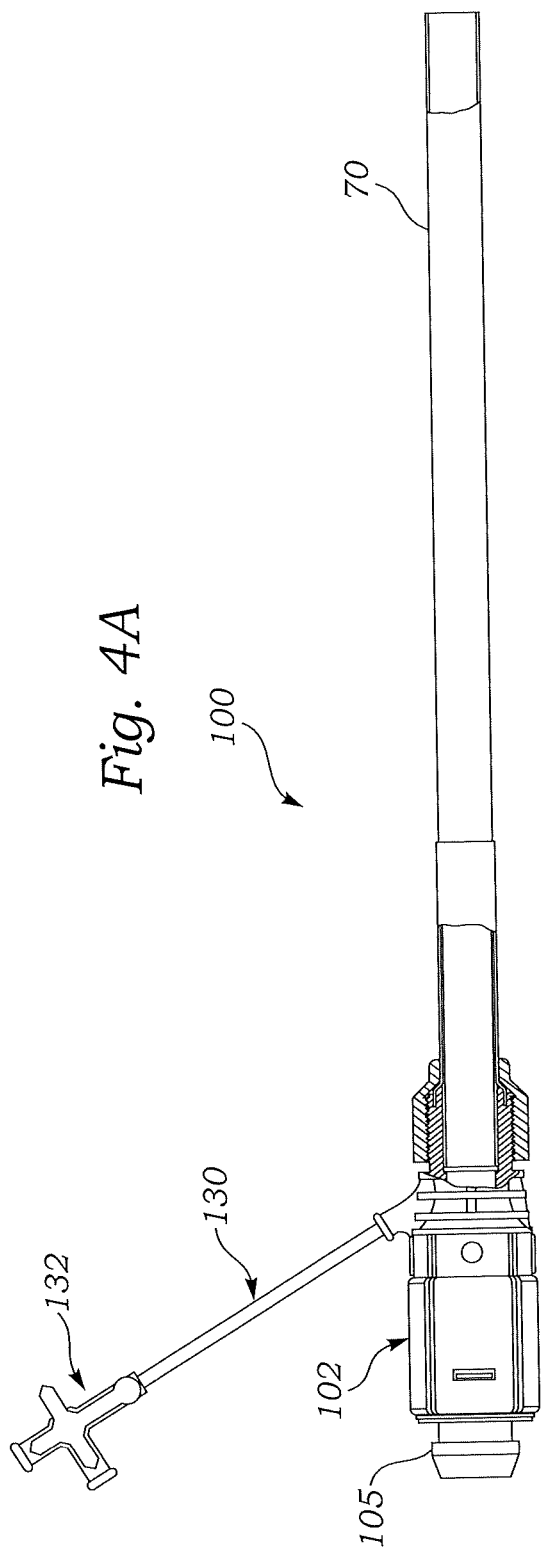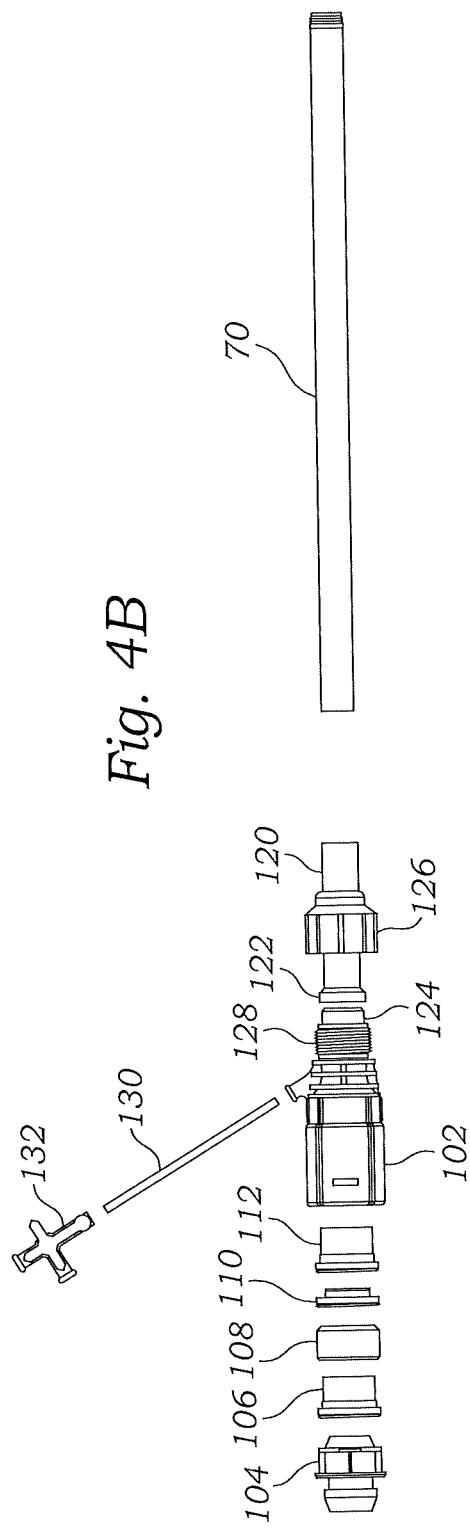

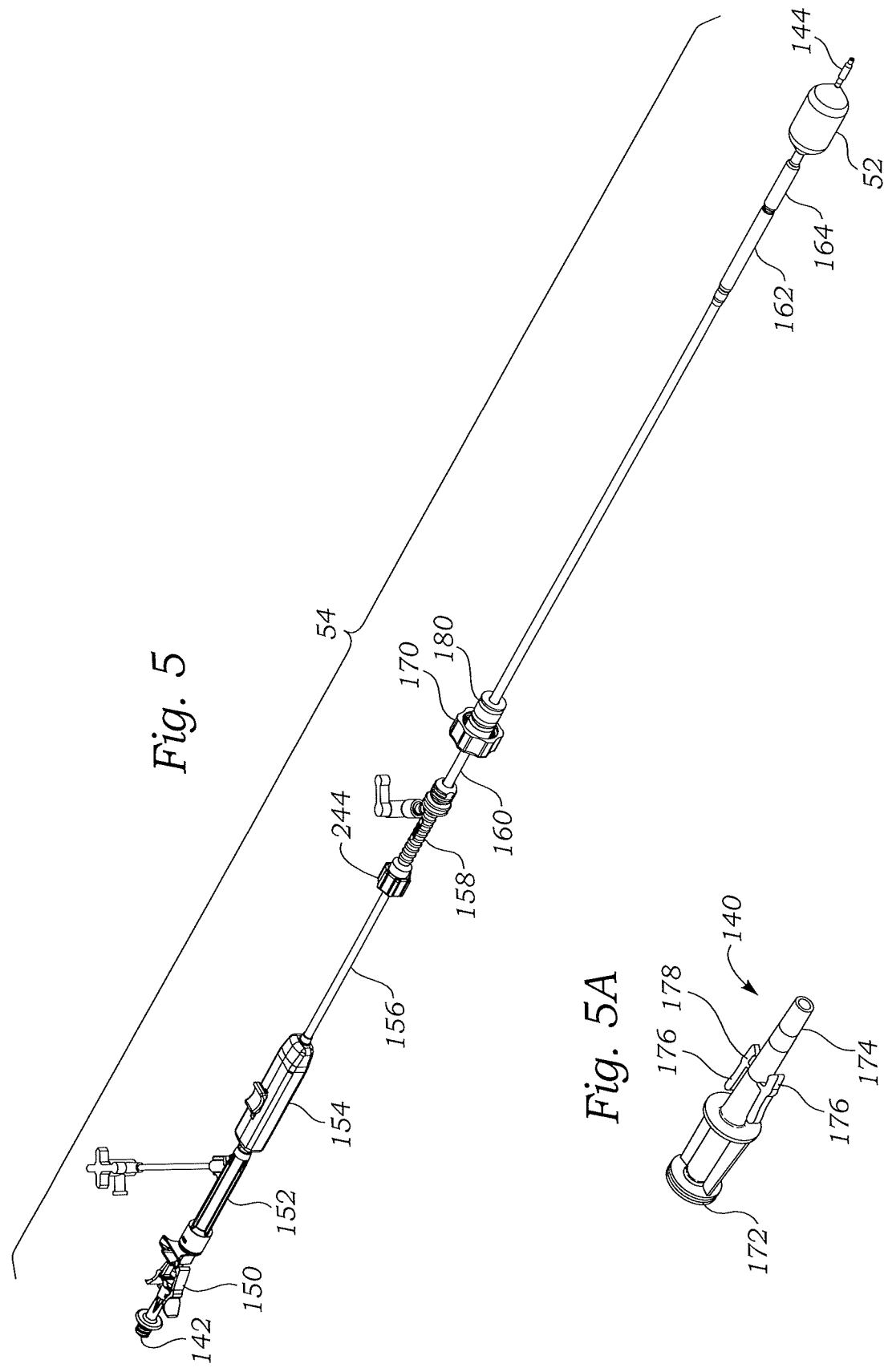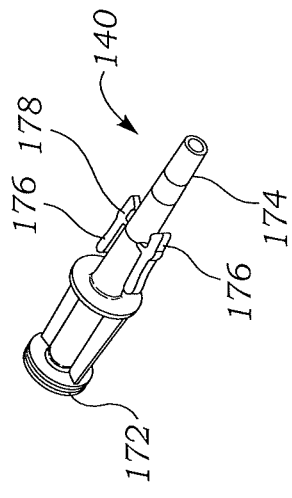

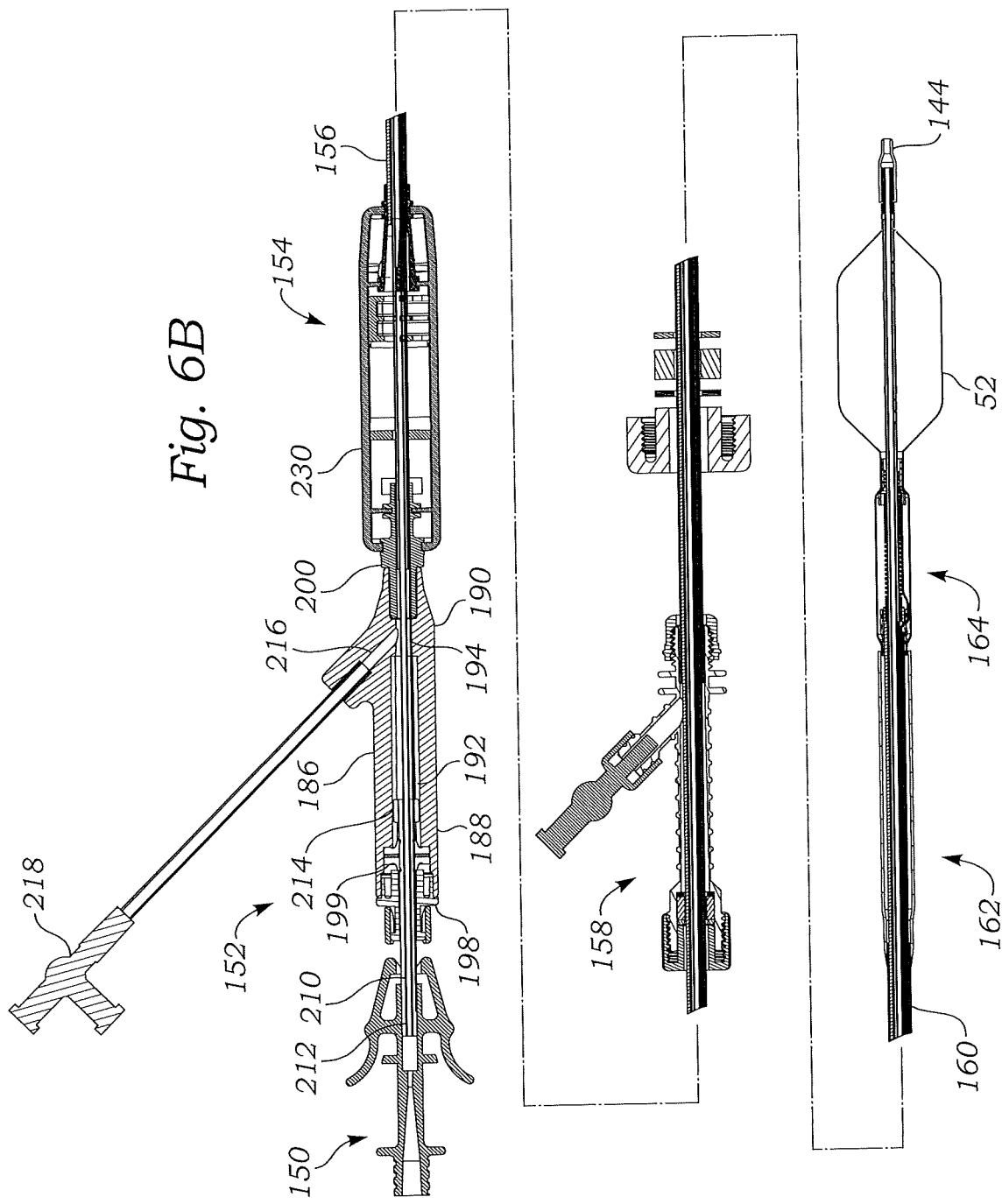

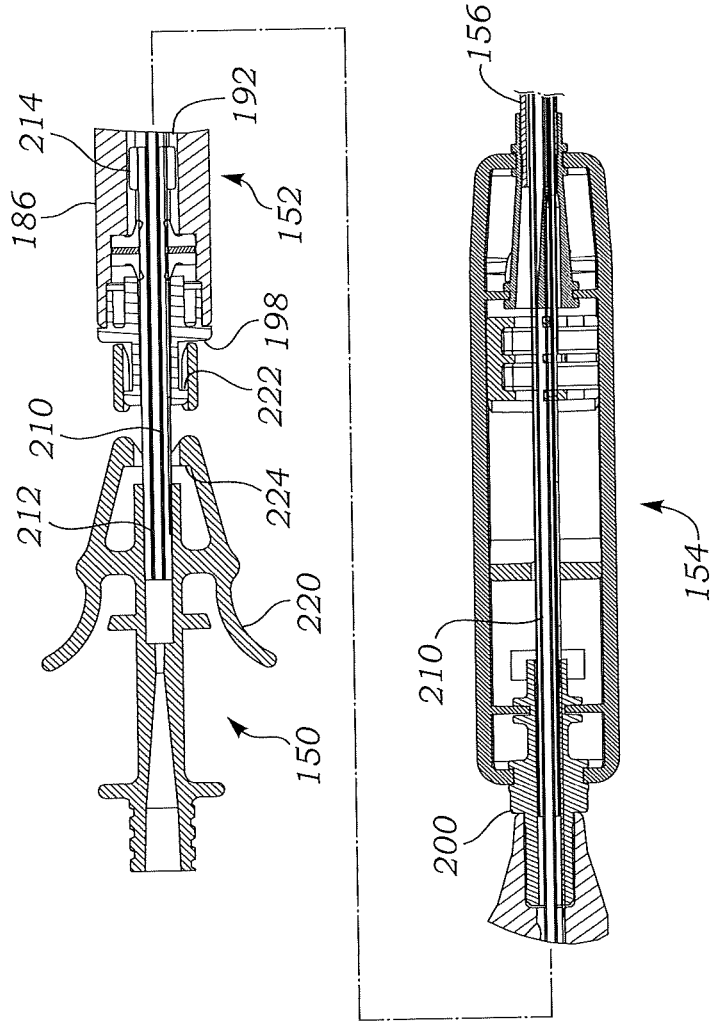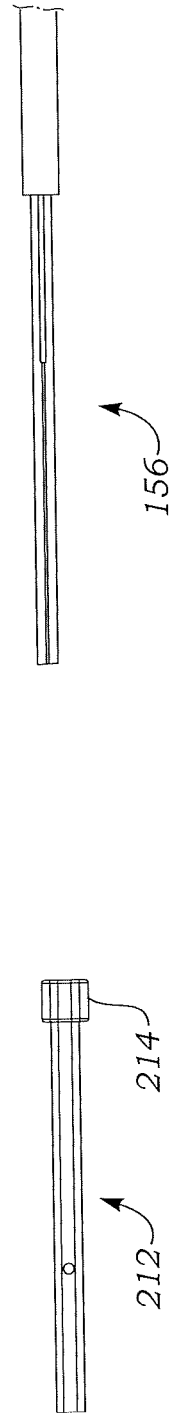

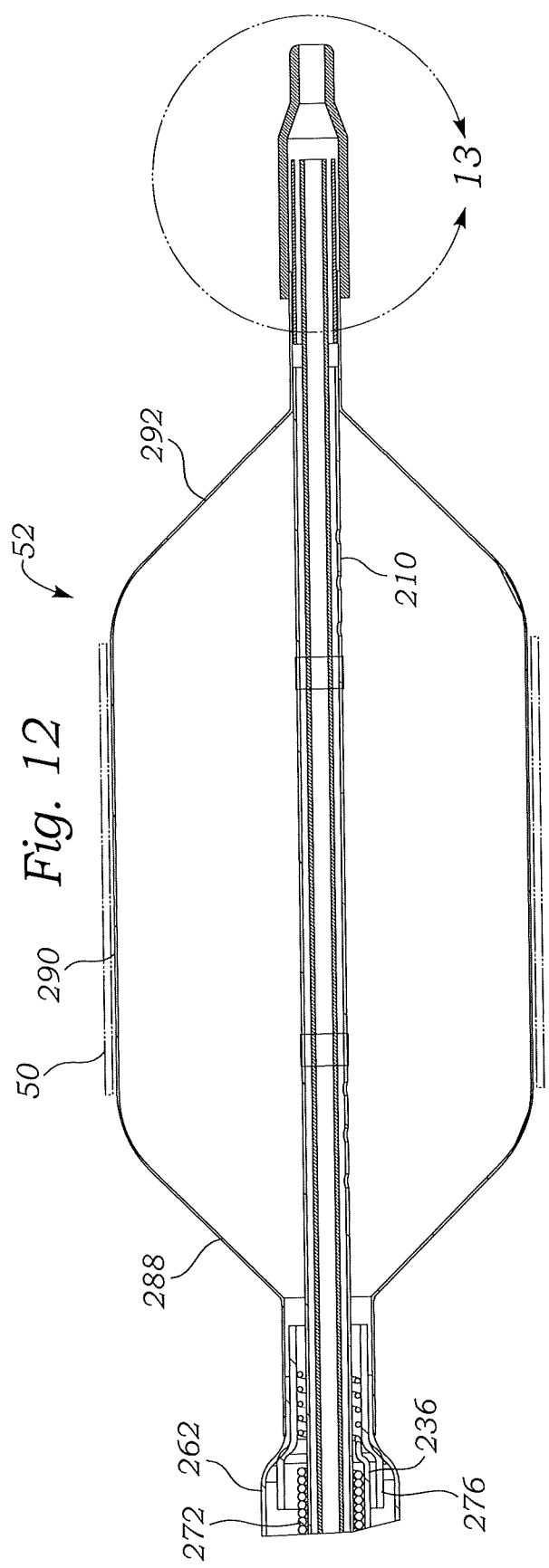
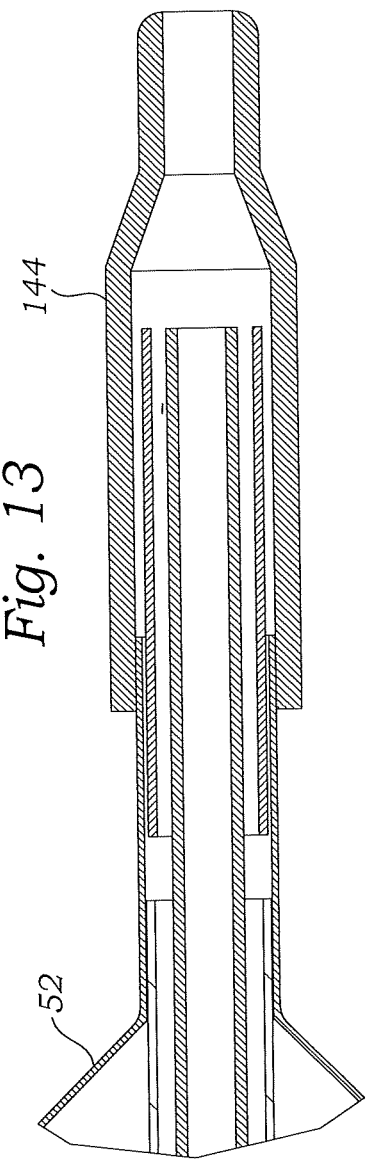

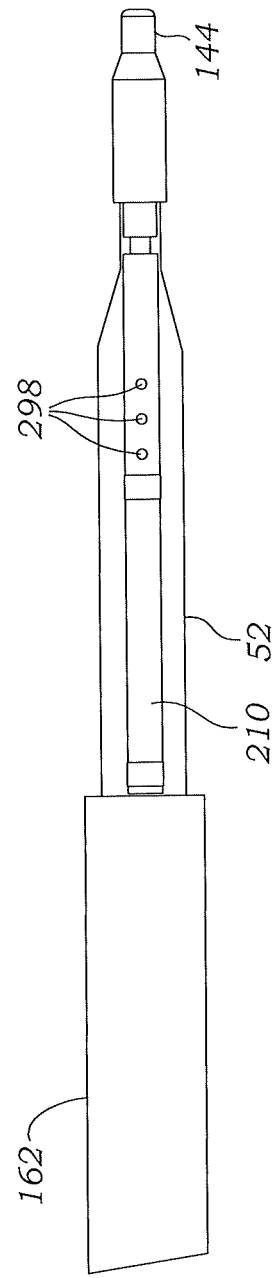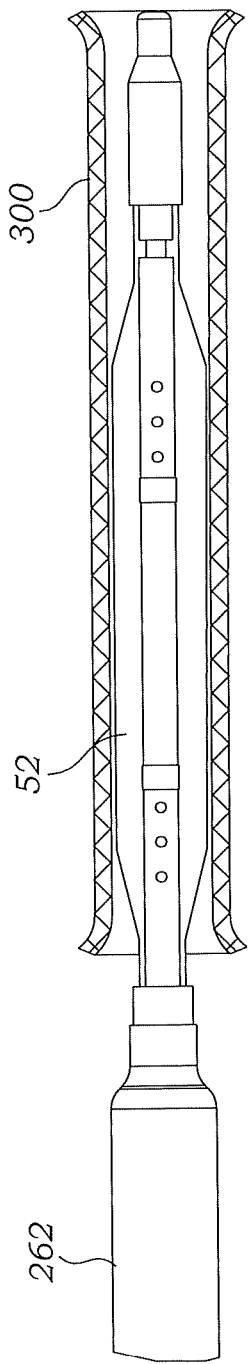

TRANSAPICAL HEART VALVE DELIVERY SYSTEM

CROSS-REFERENCE TO RELATED APPLICATION

The present application is a continuation of U.S. application Ser. No. 15/596,409, filed May 16, 2017, now U.S. Pat. No. 10,314,702, which is a continuation of U.S. application Ser. No. 14/316,390, filed Jun. 26, 2014, now U.S. Pat. No. 9,662,207, which is a continuation of U.S. application Ser. No. 11/280,063, filed Nov. 16, 2005, now U.S. Pat. No. 8,764,820, which is incorporated by reference herein.

FIELD OF THE INVENTION

The present invention relates to methods and systems used to deliver a prosthetic valve to a heart. More specifically, the present invention relates to methods and apparatus for surgically replacing a heart valve without opening the chest cavity and with or without placing the patient on bypass, the latter being termed "off-pump."

BACKGROUND OF THE INVENTION

Heart valve replacement may be indicated when there is a narrowing of the native heart valve, commonly referred to as stenosis, or when the native valve leaks or regurgitates, such as when the leaflets are calcified. When replacing the valve, the native valve may be excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart valve annulus.

Conventional heart valve surgery is an open-heart procedure conducted under general anesthesia. An incision is made through the patient's sternum (sternotomy), and the patient's heart is stopped while blood flow is rerouted through a heart-lung "cardiopulmonary" bypass machine. Valve replacement surgery is a highly invasive operation with significant concomitant risks including bleeding, infection, stroke, heart attack, arrhythmia, renal failure, adverse reactions to the anesthesia medications, as well as sudden death. Fully 2-5% of patients die during surgery. Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in "minimally-invasive" surgery and interventional cardiology have encouraged some investigators to pursue percutaneous replacement of the aortic heart valve. Percutaneous Valve Technologies ("PVT"), formerly of Fort Lee, N.J. and now part of Edwards Lifesciences of Irvine, Calif., has developed a balloon-expandable stent integrated with a bioprosthetic valve. The stent/valve device is deployed across the native diseased valve to permanently hold the valve open, thereby alleviating a need to excise the native valve. PVT's device is designed for delivery in a cardiac catheterization laboratory under local anesthesia using fluoroscopic guidance, thereby avoiding general anesthesia and open-heart surgery.

Other prior art minimally-invasive heart valves use self-expanding stents as anchors. In the percutaneous/endovascular aortic valve replacement procedure, accurate placement of the prosthetic valve relative to the coronary ostia is critical. Though the proximal end of the stent is not released from the delivery system until accurate placement is verified by fluoroscopy, the self-expanding stent may still jump once released. It is therefore often difficult to know where the ends of the stent will be with respect to the native valve and surrounding structures.

U.S. Patent Publication No. 2002/0151970 to Garrison et al. describes a two-piece device for replacement of the aortic valve that is adapted for delivery through a patient's aorta. A stent is endovascularly placed across the native valve, then a replacement valve is positioned within the lumen of the stent and connected thereto. By separating the stent and the valve during delivery, a so-called "two-stage" approach, the profile of the delivery system can be reduced. Both the stent and a frame of the replacement valve may be balloon- or self-expandable.

Some researchers propose implanting prosthetic heart valves at the aortic annulus through a ventricular approach. For instance, Christoph H. Huber of the Brigham and Women's Hospital of Harvard Medical School, and others, have proposed a procedure in which a self-expanding valve stent is implanted at the aortic position using a direct-access transapical approach. (E.g., Huber, et al. Direct-access valve replacement a novel approach for off-pump valve implantation using valved stents. J Am Coll Cardiol 2005; 46:366-70). The clinical studies by Huber, et al. recommend use of the procedure only for animals with normal, noncalcified leaflets. More recently, Bergheim in U.S. Patent Publication No. 2005/0240200 discloses another transapical approach in which either a balloon- or self-expanding valve may be implanted, and also proposes removing or decalcifying stenotic valves.

In view of drawbacks associated with previously known techniques for replacing a heart valve without open-heart surgery or cardiopulmonary bypass, i.e., minimally-invasive procedures, improved methods and apparatuses that are more robust and less invasive are needed.

SUMMARY OF THE INVENTION

Preferred embodiments of the present invention provide a heart valve delivery system for delivery of a prosthetic (i.e., replacement) heart valve to a native valve site without an open chest procedure. The delivery system includes a valve delivery catheter having a steerable section to facilitate positioning of the valve.

In accordance with one aspect, the present invention provides an off-pump, minimally-invasive surgical method of implanting a prosthetic heart valve to an aortic valve annulus of a patient while the patient's heart remains beating. The method includes providing a balloon-expandable prosthetic heart valve mounted over a balloon on a distal end of a balloon catheter. The physician creates a puncture through the ventricle wall at or near the apex of the left ventricle of the patient and inserts an introducer sheath through the puncture. A balloon catheter passes through the introducer sheath into the left ventricle. The distal end of the balloon advances so that the prosthetic heart valve is positioned within the aortic annulus. Finally, the balloon inflates to expand the prosthetic heart valve at the aortic annulus.

The method may also include placing a first line of purse-string sutures generally in a first circle in one direction defining a perimeter at or near the apex of the left ventricle of the patient, and then placing a second line of purse-string sutures generally in a circle concentric to the first circle but in an opposite direction. The puncture is created within the perimeter, and after the introducer sheath is inserted through the puncture, the purse-string sutures are cinched to create a seal therearound.

Desirably, the balloon catheter incorporates a steering mechanism, and the method further includes steering the balloon catheter within the left ventricle to facilitate positioning the prosthetic heart valve within the aortic annulus. The balloon catheter may also include a deflecting segment located just proximal to the balloon which bends so as to angle the balloon and prosthetic heart valve mounted thereon. The balloon catheter may also have a pusher with a distal sleeve mounted over the deflecting segment and engaging a proximal end of the balloon. The method therefore includes using the pusher and sleeve to advance the balloon and prosthetic heart valve mounted thereon, and proximally displacing the pusher and sleeve with respect to the deflecting segment prior to inflating the balloon. Desirably, the pusher and sleeve are proximally displaced before the deflecting segment bends.

The exemplary method may further include leaving the native aortic valve leaflets in place such that inflating the balloon expands the prosthetic heart valve into contact therewith. Furthermore, a pre-dilation balloon catheter may be inserted prior to the introducer sheath and a balloon thereon inflated to pre-dilate the aortic annulus. Alternatively, the method may include expanding the prosthetic heart valve into contact with a prosthetic heart valve that was previously implanted at the aortic annulus Another off-pump, minimally-invasive surgical method of delivering a prosthetic heart valve to an aortic valve annulus of a patient while the patient's heart remains beating includes providing an expandable prosthetic heart valve in an expanded state and a delivery catheter having a distal end. The heart valve is crimped to a contracted state over the delivery catheter distal end. An intercostal access opening is created to expose the left ventricular apex of the patient, and a puncture formed at or near the apex of the left ventricle. An introducer sheath inserts through the puncture, and the delivery catheter passes through the introducer sheath and into the left ventricle. The distal end of the delivery catheter is advanced and steered so that the prosthetic heart valve is properly positioned and oriented within the aortic annulus. Finally, the prosthetic heart valve expands at the aortic annulus into contact therewith.

The delivery catheter desirably includes a balloon on its distal end, and the prosthetic heart valve includes a balloon-expandable stent, wherein the step of expanding includes injecting fluid into the balloon to expand the prosthetic heart valve outward into contact with the aortic annulus. The native aortic valve leaflets may be left in place such that inflating the balloon expands the prosthetic heart valve into contact therewith. Preferably, prior to inserting the introducer sheath, a pre-dilation balloon catheter having a balloon on a distal end is inserted through the puncture and inflated to pre-dilate the aortic annulus.

The present invention further encompasses a minimally-invasive prosthetic heart valve delivery system, including an introducer sheath having a lumen therethrough of no greater than 24 French and a balloon catheter having a balloon on a distal end, the balloon catheter further including a steering mechanism for deflecting the distal end. The system includes a balloon-expandable prosthetic heart valve crimped over the balloon, wherein the outer dimension of the balloon catheter with the prosthetic heart valve crimped thereon is small enough to pass through the introducer sheath lumen.

Desirably, the steering mechanism includes a deflecting segment on the balloon catheter located just proximal to the balloon. A deflection wire may be attached to a distal end of the deflecting segment and extend through the balloon catheter to a proximal deflection handle. The system preferably has a pusher with a distal sleeve sized to encompass the deflecting segment and a proximal end of the balloon, the pusher being longitudinally movable with respect to the deflecting segment.

In one embodiment, the balloon catheter further includes inner and outer balloon inflation tubes attached to opposite ends of the balloon and arrange to concentrically slide with respect one another to alternately elongate and shorten the balloon. An inner tube handle displaces the inner balloon inflation tube. A balloon inflation connector through which the inner balloon inflation tube passes attaches to a proximal end of the outer balloon inflation tube. A side port opens to a space defined within the balloon inflation connector, the side port facilitating introduction of an inflation fluid into the space and into a tubular space between the inner and outer balloon inflation tubes for inflating the balloon. A deflection handle through which the outer balloon inflation tube passes may be attached just distal to the balloon inflation connector. The outer balloon inflation tube includes a first lumen for passage of the inner balloon inflation tube, and a second lumen. A deflection wire connects to an actuator on the deflection handle and passes through the second lumen of the outer balloon inflation tube to a distal end of the balloon catheter.

The system is desirably relatively short, such that the balloon catheter has a working length sized to fit into the introducer of no more than about 24 inches (61 cm). At the same time, the introducer preferably has a total length of no more than about 13 inches (33 cm).

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 3A-3E are cross-sectional views through the left side of a patient's heart showing several steps in a procedure for implanting a prosthetic heart valve in accordance with the present invention;

FIG. 4A is a side elevational view of an introducer used in the minimally-invasive heart valve implantation procedure of the present invention;

FIG. 4B is an exploded view of the introducer of FIG. 4A;

FIG. 5 is a perspective view of an exemplary balloon catheter for implanting a prosthetic heart valve in accordance with the present invention;

FIG. 5A is a perspective view of a loader that provides an interface between the introducer of FIG. 4A and the balloon catheter of FIG. 5;

FIG. 6B is an enlarged broken sectional view of the balloon catheter of FIG. 5 taken along a vertical plane;

FIG. 7 is an enlarged broken portion of the proximal end of the balloon catheter as seen in FIG. 6B;

FIG. 8 is an isolated side view of a tube segment having an anti-rotation block on one end that forms part of the balloon catheter of FIG. 5;

FIG. 9 is an isolated side view of a proximal end of an outer balloon inflation tube that forms part of the balloon catheter of FIG. 5;

FIG. 12 is an enlarged sectional view of the distal balloon of the balloon catheter of the present invention in its expanded state;

FIG. 13 is an enlarged sectional view of a distal soft tip of the balloon catheter;

FIG. 14 is an enlarged elevational view of the distal end of the balloon catheter showing the balloon in its deflated state partly encompassed by a pusher sleeve; and FIG. 15 is an enlarged elevational view of the distal end of the balloon catheter showing a protective sheath around the deflated balloon.

DETAILED DESCRIPTION OF THE PREFERRED EMBODIMENTS

The heart is a hollow muscular organ of a somewhat conical form; it lies between the lungs in the middle mediastinum and is enclosed in the pericardium. The heart rests obliquely in the chest behind the body of the sternum and adjoining parts of the rib cartilages, and projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles.

Figure 1:
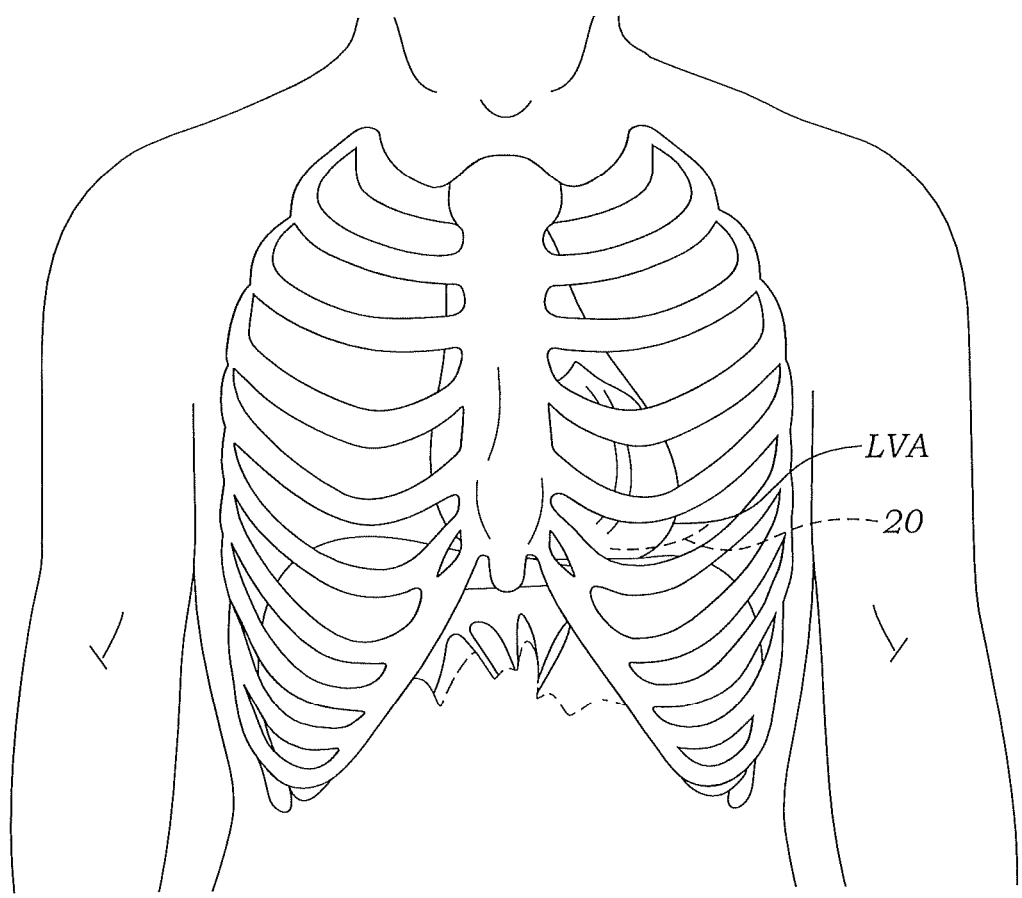
FIG. 1 is a schematic frontal view of a patient showing the location of an intercostal incision providing access to the apex of the left ventricle of the heart.

As seen in FIG. 1, the left ventricular apex LVA is directed downward, forward, and to the left (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision 20 as shown in dashed line, positioned over the fifth left intercostal space. Such an approach is often termed a "mini-thoracotomy."

In a preferred embodiment of the present invention, a surgeon implants a prosthetic heart valve over the existing native leaflets, which are typically calcified. There are procedures and devices for removing calcified leaflets, but the risks associated therewith, including a release of calcific material into the bloodstream, are not insignificant. Therefore, a heart valve replacement procedure that installs the prosthetic heart valve directly over and contains the native leaflets is preferred.

Figure 2A:
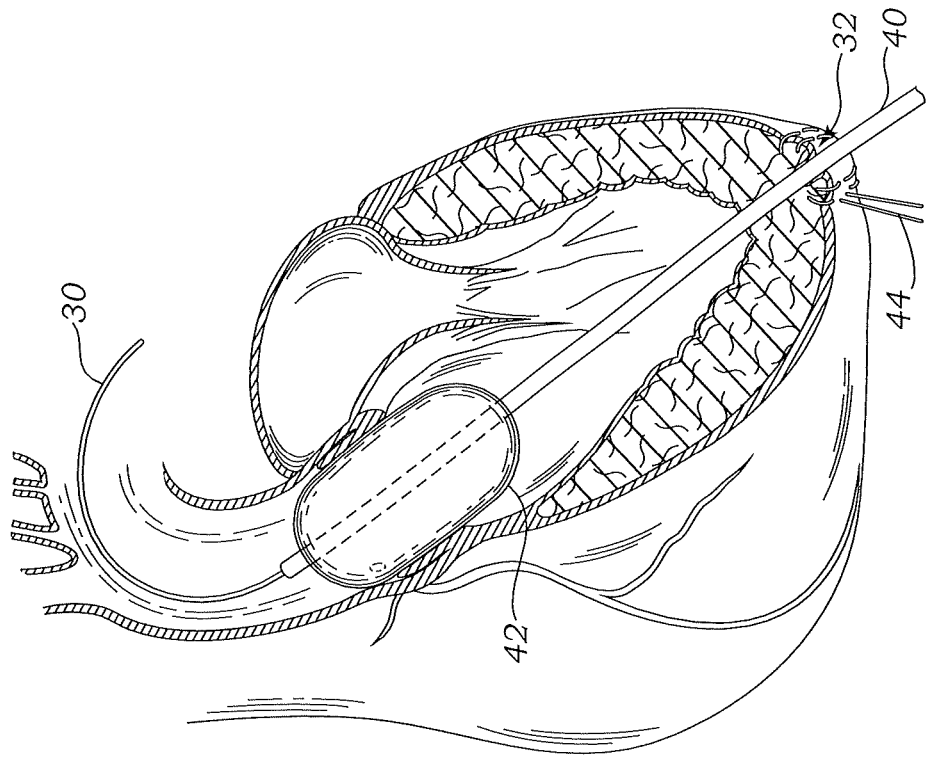
FIGS. 2A-2B are cross-sectional views through the left side of a patient's heart showing a procedure for dilating a calcified aortic annulus prior to implantation of a prosthetic heart valve in accordance with the present invention.
Figure 2B:
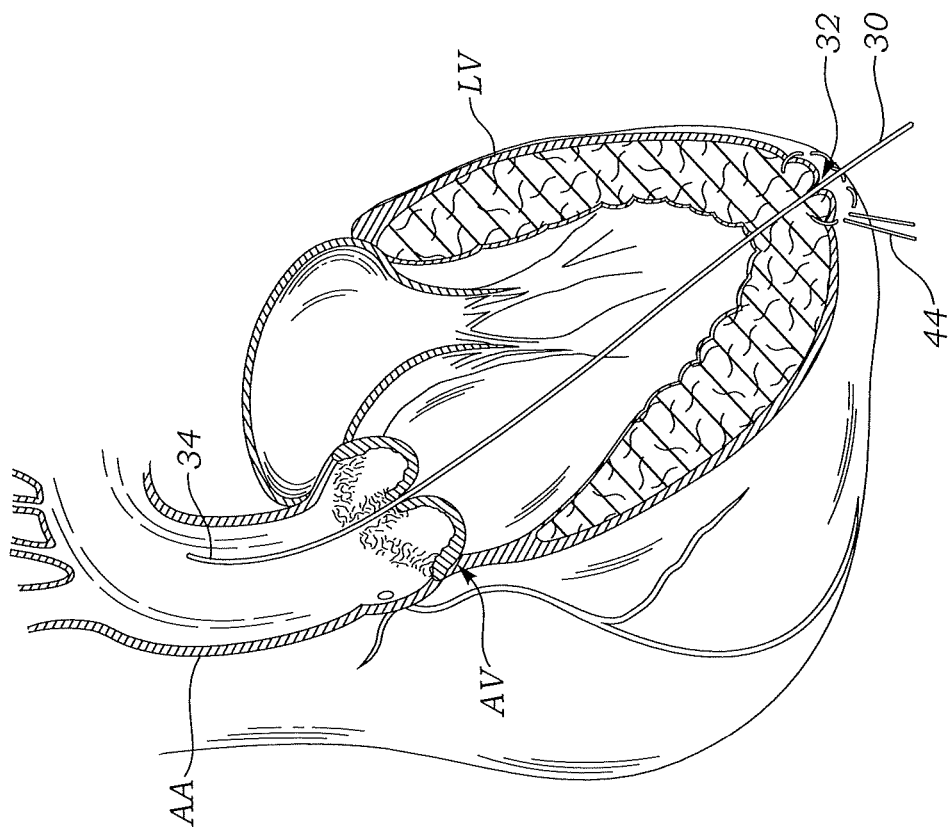

Those skilled in the art will recognize that it may be necessary to pre-dilate the leaflets and annulus of the stenotic aortic valve before deploying a prosthetic valve within the aortic valve. FIGS. 2A and 2B are two snapshots of a valvuloplasty procedure that may be initially performed to compress the native aortic heart valve leaflets outward against the sinuses and ascending aorta. As mentioned above, the native aortic valve leaflets may be substantially calcified, and the valvuloplasty may be necessary to crack and otherwise force apart hardened tissue. Pre-dilation increases the flow area through the aortic valve and creates an opening in the leaflets of sufficient size to receive the prosthetic valve. Pre-dilatation is preferably achieved using an expandable member, such as a dilatation balloon catheter. One example of pre-dilation of a valve annulus is seen in U.S. Pat. No. 6,908,481 to Cribier, issued Jun. 21, 2005 and expressly incorporated by reference herein.

FIG. 2A illustrates introduction of a guidewire 30 through an apical puncture 32 in the left ventricle LV. A distal tip 34 of the guidewire 30 extends through the native aortic valve AV and into the ascending aorta AA. The distal tip 34 may extend further over the aortic arch, as seen in FIG. 2B, but the minimum extension is across the aortic valve AV.

FIG. 2B illustrates a balloon catheter 40 having a dilatation balloon 42 on a distal end passed over the guidewire 30 and through the apical puncture 32. It should be noted at this point that one or more purse-string sutures 44 are threaded through the tissue of the left ventricular apex surrounding the puncture 32. These sutures 44 are pre-implanted prior to formation of the initial puncture. In a preferred embodiment, the surgeon places a first line of purse-string sutures generally in a first circle in one direction, and then places a second line of purse-string sutures generally in a circle concentric to the first circle but in an opposite direction. The result is two concentric circles of separate purse-string sutures 44 defining a periphery within which the puncture is formed. The purse-string sutures 44 can therefore be pulled to cinch the ventricular tissue around whatever object passes through the puncture. In particular, the purse-string sutures 44 are tightened around both the guidewire 30 and balloon catheter 40. Installing the separate lines of purse-string sutures 44 in opposite directions helps prevent tearing of the ventricular tissue and provides a more uniform compression about whatever elongated object passes through the puncture.

As indicated in FIG. 2B, the dilatation balloon 42 expands radially outward into contact with the native aortic valve leaflets. With information concerning the size of the particular aortic valves, the balloon 42 is chosen so that it expands outward and nominally compresses the aortic valve leaflets against the surrounding aortic walls. There are various means for assessing the size of the particular patient's aortic valve, including ultrasound, which will not be described herein. Suffice it to say that following the valvuloplasty procedure seen in FIG. 2B, the native aortic valve leaflets are compressed outward against the aortic wall and a substantially circular orifice results. Additional details regarding pre-dilatation and valve replacement can be found in Applicant's U.S. Pat. No. 6,908,481, filed May 2, 2002, and expressly incorporated by reference herein.

With reference now to FIGS. 3A-3E, a preferred method of deploying and implanting a prosthetic heart valve of the present invention using a transapical approach will now be described in more detail. The devices and methods disclosed herein are particularly well-suited for replacing a stenotic aortic valve, and as such that the pre-dilation procedure seen in FIGS. 2A-2B typically precedes the valve implantation so as to smooth out the contours of the annulus and leaflets. It should be noted, however, that the procedure described herein may be performed without valve pre-dilation.

Furthermore, the present procedure may be performed as a first time valve implant or to supplement a previous implant. A relatively large proportion of recipients of prosthetic heart valves are older, typically older than 60. Over time, prosthetic heart valves have been known to show reduced performance and even failure. Re-operating on septuagenarians and even octogenarians is problematic. However, a minimally-invasive procedure such as disclosed herein eliminates open-heart surgery and potentially cardiopulmonary bypass, and is therefore more desirable for the aging patient. Therefore, the present invention contemplates transapical implantation of a prosthetic heart valve over an existing prosthetic valve implant. In such a case, a pre-dilation step is typically not necessary, though it is conceivable.

Prior to a discussion of the procedure itself, it should be noted that a preferred delivery system of the present invention will be described in greater detail below with reference to FIGS. 4-15. The workings of the present delivery system may be more easily understood after an explanation of the steps taken to ultimately implant the valve in the aortic annulus.

The prosthetic heart valve implantation procedure described herein may be performed in conjunction with cardiopulmonary bypass, or without in a so-called off-pump procedure. The necessity for bypass depends on a number of factors, including the patient's age, vulnerability to such a procedure, and viability of the native leaflets. Ideally, the implantation procedure is performed off-pump.

The surgeon or cardiologist first sizes the aortic valve using a physical sizer, or echocardiography. The physician or operating room staff then crimps an expandable prosthetic valve 50 over the balloon 52 of a balloon catheter 54 (some of the elements presently described can be seen in the procedure drawings of FIGS. 3A-3E, while others can be seen in the system drawings of the FIGS. 4-15). The surgeon advances the balloon catheter 54 over a guidewire 60 (that might be the same guidewire 30 used in a pre-dilation procedure), through an introducer sheath 70 that has been inserted through the left ventricular apex puncture 32.

The same purse-string sutures 44 that were used for the pre-dilation procedure may also be used to seal the ventricular tissue around the introducer sheath 70. In the absence of the pre-dilation procedure, the purse-string sutures 44 are pre-implanted prior to formation of the initial puncture. As before, the surgeon places a first line of purse-string sutures generally in a first circle in one direction, and then places a second line of purse-string sutures generally in a circle concentric to the first circle but in an opposite direction. The result is two concentric circles of separate purse-string sutures 44 defining a periphery within which the puncture is formed, and which seal around the introducer sheath 70.

Furthermore, a dilator (not shown) that expands the inner diameter of the puncture 32 and rides over the guidewire 60 may be inserted prior to the introducer sheath 70. Preferred dilator diameters range between 12 and 22 French. The introducer sheath 70 comprises the distal end of an introducer that will be described below. Introducer sheath diameters of no greater than 24 French, and desirably 22 or 24 Fr are preferred.

Figure 3A:
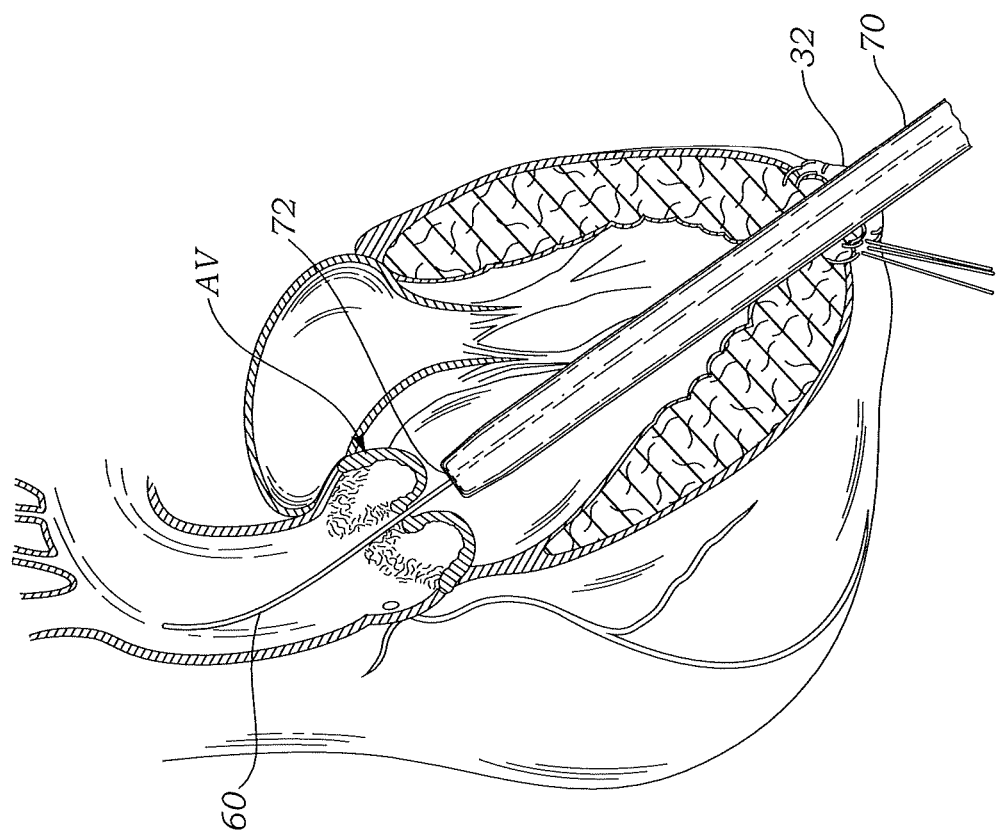

FIG. 3A shows the introducer sheath 70 passing into the left ventricle through the puncture 32 and over the guidewire 60 that extends upward through the calcified aortic valve AV. The surgeon locates a distal tip 72 of the introducer sheath 70 just to the inflow side of the aortic valve AV, as seen in FIG. 3A. At this point, it should be understood by those of skill in the art that the position of the introducer sheath 70 relative to the aortic valve AV, as well as the position of other elements of the system, is monitored using radiopaque markers and fluoroscopy, or using other imaging systems such as transesophageal echo, transthoracic echo, intravascular ultrasound imaging (IVUS), or an injectable dye that is radiopaque.

FIG. 3B shows the advancement of the balloon catheter 54 over the guidewire 60 and through the introducer sheath 70. Ultimately, as seen in FIG. 3C, the prosthetic heart valve 50 is located at the aortic annulus and between the native aortic leaflets. FIG. 3C also illustrates retraction of the introducer sheath 70 from its more forward position in FIG. 3B. Radiopaque markers may be provided on the distal end of the introducer sheath 72 more accurately determine its position relative to the valve 50 and balloon 52.

Again, the precise positioning of the prosthetic heart valve 50 may be accomplished by locating radiopaque markers on its distal and proximal ends. Desirably, the surgeon can adjust the position of the valve 50 by actuating a steering or deflecting mechanism within the balloon catheter 54, as will be described below. Furthermore, the rotational orientation of the valve 50 can be adjusted relative to the cusps and commissures of the native aortic valve by twisting the balloon catheter 54 from its proximal end and observing specific markers on the valve (or balloon catheter) under fluoroscopy. One of the coronary ostia 80 opening into one of the sinuses of the ascending aorta is shown, and those of skill in the art will understand that it is important not to occlude the two coronary ostia with the prosthetic valve 50. It should also be noted that although the native leaflets of the aortic valve AV are shown coapting in FIG. 3A, and being flexibly displaced by the balloon catheter 54 in FIGS. 3B and 3C, they may actually be compressed further outward against the aortic annulus from a pre-dilation procedure.

Figure 3E:
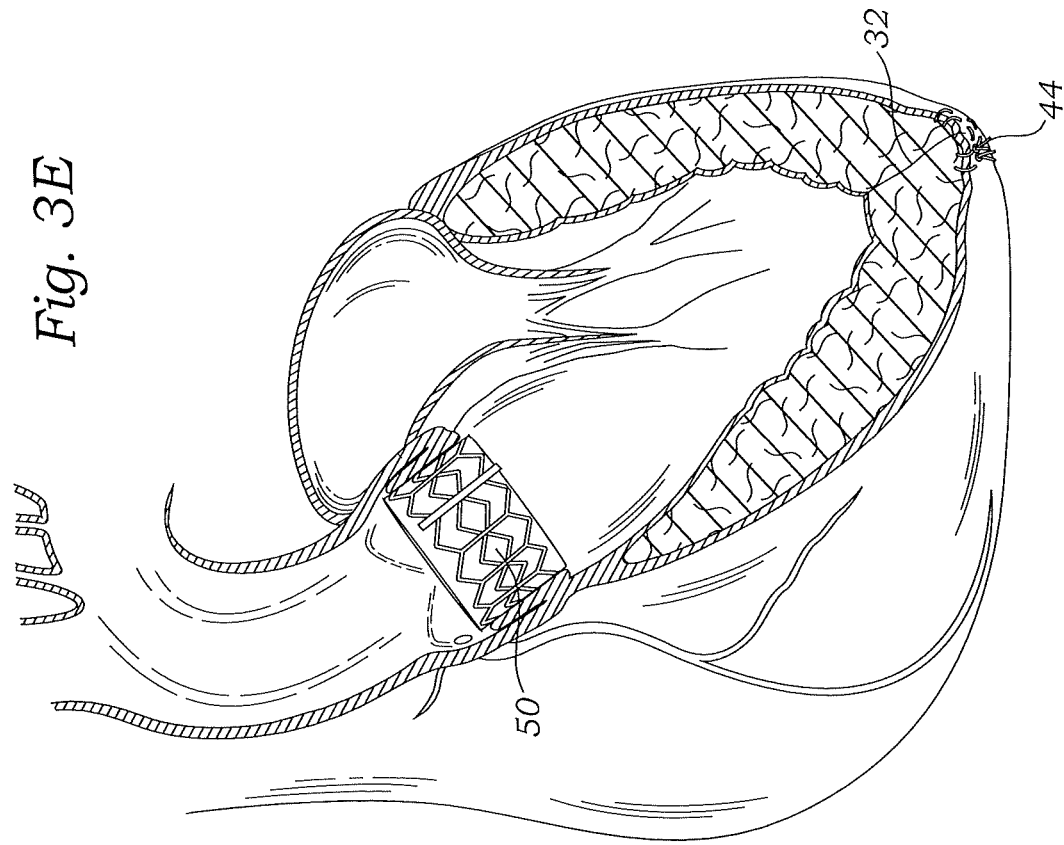
Figure 3D:
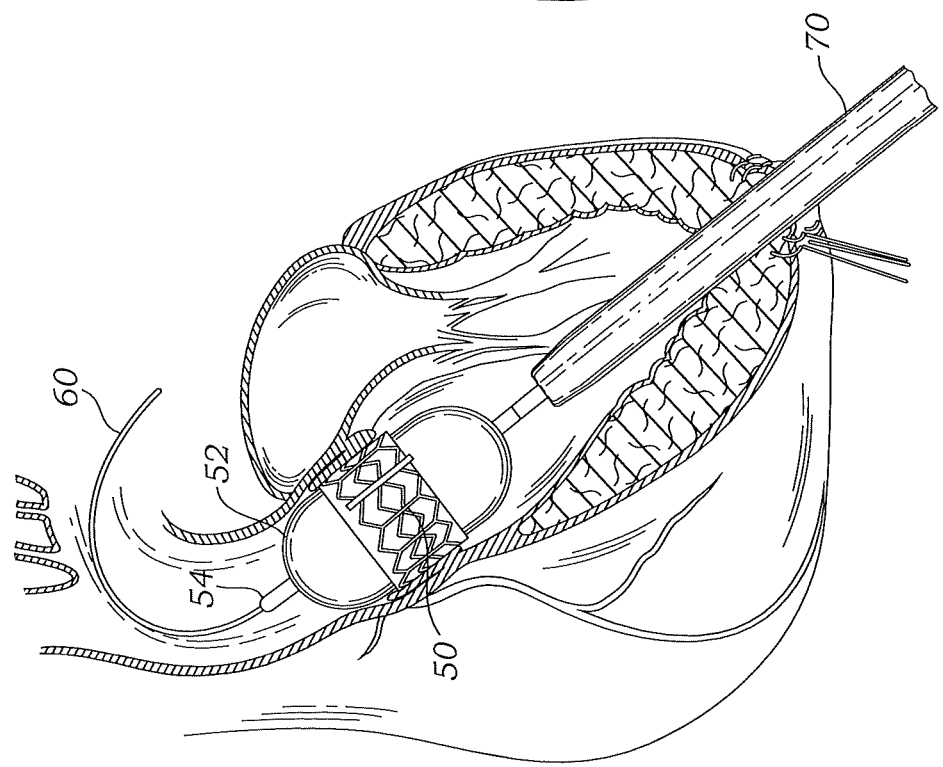

FIG. 3C shows the prosthetic heart valve 50 in its contracted or unexpanded state crimped around the balloon 52. When the surgeon is satisfied of the proper positioning and rotational orientation of the valve 50, the balloon 52 is expanded as seen in FIG. 3D. Proper size measurement of the native aortic valve AV enables the surgeon to select an optimum-sized valve 50 such that it expands outward into good contact with the aortic annulus. The term "good contact" implies sufficient contact to ensure that the prosthetic heart valve 50 does not migrate after implant. Excessive expansion of the valve, however, may damage surrounding tissue or interfere with the performance of adjacent valves.

A number of devices are available to assist in anchoring the prosthetic valve 50 into the aortic annulus, such as barbs and the like. A preferred configuration of prosthetic heart valve 50 for use with the present invention is disclosed in co-pending U.S. Pat. No. 7,276,078, filed Jun. 30, 2004, which disclosure is expressly incorporated herein by reference. Of course, the valve 50 can take a variety of different forms but generally comprises an expandable stent portion that supports a valve structure. The stent portion has sufficient radial strength to hold the valve at the treatment site and resist recoil of the stenotic valve leaflets. Additional details regarding preferred balloon expandable valve embodiments can be found in U.S. Pat. Nos. 6,730,118 and 6,893,460, both of which are expressly incorporated herein by reference. The preferred prosthetic heart valve 50 includes sufficient irregularity on its outer surface such that it may be anchored in the aortic annulus without the use of barbs or other tissue piercing structure.

Once the valve 50 is properly implanted, as seen in FIG. 3D, the balloon 52 is deflated, and the entire delivery system including the balloon catheter 54 is withdrawn over the guidewire 60. The guidewire 60 is then withdrawn, followed by the introducer sheath 70. Ultimately, the purse-string sutures 44 previously described are cinched tight and tied to close the puncture 32, as seen in FIG. 3E It is important to recognize that the heart valve delivery system of the present invention is particularly well-suited for the antegrade, left ventricular apex, "transapical," approach. More particularly, the mini-thoracotomy approach requires relatively short instruments. Therefore, the portion of the introducer sheath 70 that extends into the body is desirably no more than about 8 inches (20 cm) long, and the length of the balloon catheter 54 that may extend into the introducer sheath 70, i.e., the "working length," is desirably no more than about 24 inches (61 cm). Further specifics on the relatively short length of the balloon catheter 54 and introducer sheath 70 will be provided below. The short length of the prosthetic heart valve delivery system described herein is also well-suited for other anatomical approaches, including through the carotid or subclavian arteries. The short length of the system is desirable because it enhances controllability and steerability of the distal end, relative to longer systems, which helps improve accuracy and reduced time for valve positioning.

The delivery system of the present invention essentially comprises an introducer 100, the balloon catheter 54, and attendant couplers and operating structures, including a loader 140 between the introducer and balloon catheter as seen in FIG. 5A. The introducer 100 is illustrated in FIGS. 4A and 4B, while the balloon catheter 54 and loader 140 are shown in FIGS. 5-15. It should be noted that the delivery system is similar to another system used to percutaneously implant a prosthetic aortic valve, which is disclosed in co-pending U.S. Pat. No. 7,780,723, filed Jun. 13, 2005, and expressly incorporated herein by reference. The present system differs in several aspects that make it more suitable for a transapical approach, although some features are common.

As seen in FIGS. 4A and 4B, the introducer 100 comprises the aforementioned distal sheath 70 coupled to an introducer housing 102 containing a series of valves. The exploded view of FIG. 4B shows an end cap 104 detached from the introducer housing 102. The end cap 104 includes a flanged nipple 105 for mating with the loader 140, as will be explained below. The end cap 104 threads or otherwise attaches to the housing 102 and retains therein, in series from proximal to distal, a cross-slit valve 106, a spacer 108, a disk valve 110, and a duck-bill valve 112. These three valves function to provide a seal when no instruments pass through the introducer 100, and when several different sizes of instruments pass therethrough. For example, the valves seal around both the guidewire 60 and the balloon catheter 54 as previously shown. The introducer sheath 70 extends into the body vessel, with the introducer housing 102 located outside the body vessel. In a preferred embodiment, the introducer sheath 70 possesses an external hydrophilic coating and has a length of about 8 inches so that it may extend through the access incision 20 (see FIG. 1), into the left ventricle and reach the aortic annulus.

The introducer sheath 70 attaches to the housing 102 via an intermediate section of tubing 120. The tubing 120 is desirably size slightly larger than the sheath 70 such that it can be shrunk around a proximal end thereof. The proximal end of the tubing 120 includes a sealing flange 122 that mates with a distal nipple 124 extending from the housing 102. Preferably adhesive is used between these two mating sections. A nut housing 126 rides over the tubing 120 and couples to threading 128 provided on the housing 102 just proximal to the nipple 124. In this way, the various components can be manufactured (typically molded or extruded) separately and easily coupled together during assembly.

A side port tube 130 extends at an angle away from the introducer housing 102 and terminates in a three-way stopcock 132. This permits the user to infuse medicaments or other fluids through the lumen of the introducer 100 even if devices such as the balloon catheter 54 are present therein.

FIG. 5 illustrates in perspective the balloon catheter 54, which comprises an assembly of interrelated components commencing on a proximal end with a luer fitting 142 and terminating at a distal end in a soft tip 144. The loader 140 shown in perspective in FIG. 5A will be described in more detail below and provides a coupling between the balloon catheter 54 and the above-described introducer 100. The balloon catheter 54 is also shown in plan, sectional, and isolated views in FIGS. 6-15 and comprises, from proximal to distal, an inner tube handle 150 having the luer fitting 142, a balloon inflation connector 152, a deflection handle 154, an outer balloon inflation tube 156, a pusher handle 158, a pusher body 160, a pusher sleeve 162, a deflecting segment 164, and an expandable balloon 52 located just proximal to the soft tip 144. An internally threaded loader cap 170 fits over the pusher body 160 and couples to the loader 140.

Figure 6A:
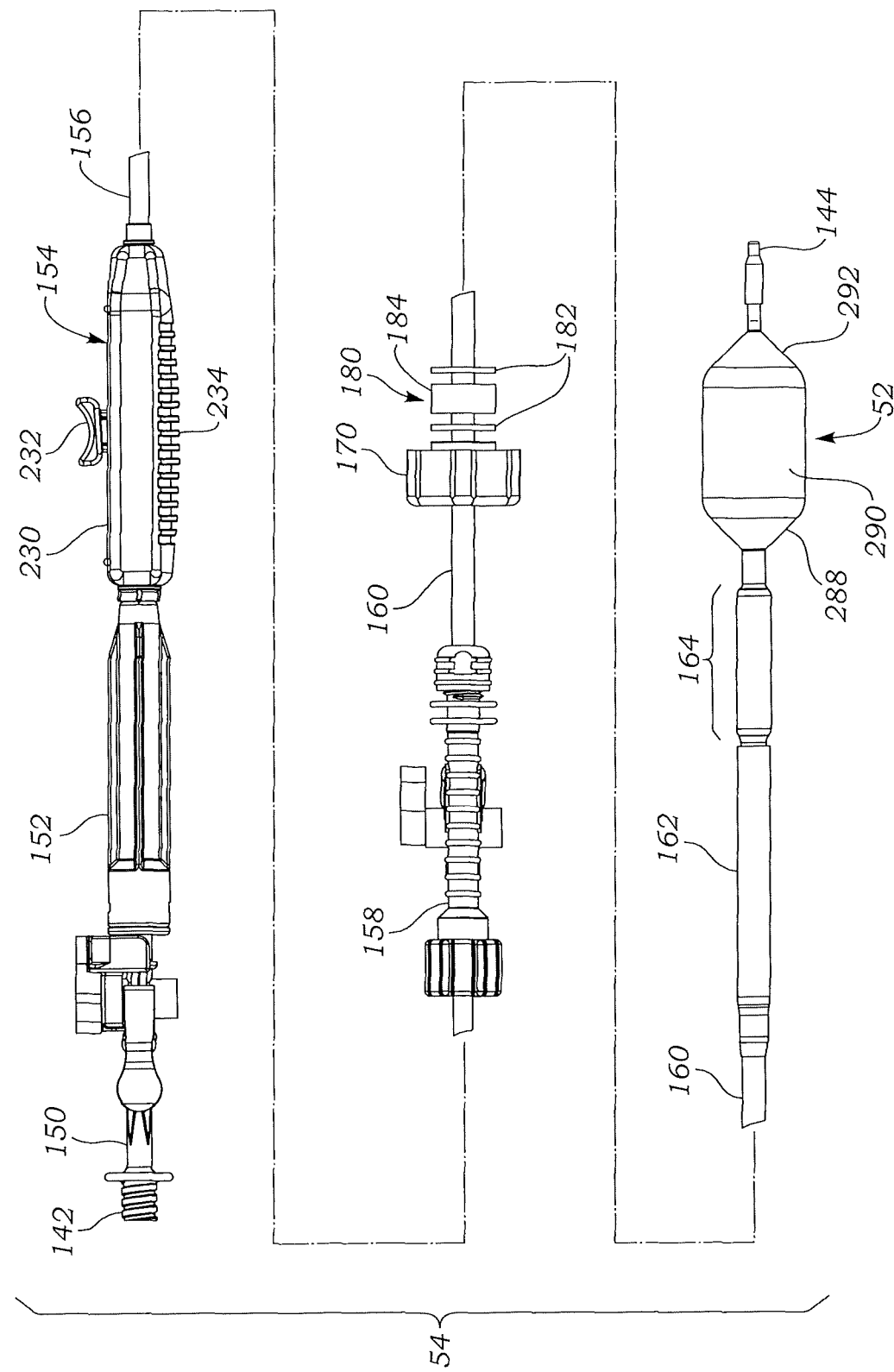
FIG. 6A is an enlarged broken plan view of the balloon catheter of FIG. 5.

Prior to a detailed description of the exemplary balloon catheter 54, its interaction with the introducer 100 via the loader 140 will be explained. The loader 140 has a tube-shaped body with exterior threading 172 at a proximal end for connection with internal threading on the loader cap 170, and a slightly externally tapered distal nose 174 that fits within the introducer 100. The loader 140 includes a pair of attached cantilevered fingers 176 extending parallel thereto with internally facing snap ridges 178 for securing the loader 140 to the introducer 100. An annular loader seal 180, seen better in FIGS. 6A and 6B, is positioned within the loader cap 170. The annular loader seal 180 comprises a pair of annular washers 182, preferably nylon, that sandwich therebetween an annular resilient seal 184, preferably silicone.

The loader 140 facilitates introduction of the balloon catheter 54 into the introducer 100. As described above, the introducer housing 102 contains the series of valves 106, 110, 112 that in aggregate provide an effective fluid seal against egress of blood through the introducer 100 in the absence or presence of different sized medical implements. The distal nose 174 of the loader 140 extends through the introducer housing 102 and through these valves 106, 110, 112 to hold them open and provide a smooth internal lumen which matches the size of the lumen of the introducer sheath 70. In this way, the somewhat irregular contours of the balloon catheter 54 having a prosthetic valve 50 crimped around the balloon 52 may smoothly pass into the introducer sheath 70.

Prior to balloon expansion as seen in FIG. 5, the loader 140 couples over the distal extent of the balloon catheter 54 and is displaced proximally until it can be coupled with the loader cap 170. Screwing the loader cap 170 onto the external threats 172 of the loader 140 axially compresses the loader seal 180 to provide a fluid tight fit and lock the loader 140 with respect to the balloon catheter 54. At this point, the distal extremity of the balloon catheter 54, including the balloon 160, is located within the tubular body of the loader 140. The distal nose 174 inserts into the introducer housing 102 and the cantilevered loader fingers 176 mate with the flanged nipple 105 of the end cap 104 (FIG. 4A). The balloon catheter 54 is thus coupled to the introducer 100. The loader cap 170 is then loosened, permitting axial displacement of the balloon catheter 54 with respect to the loader 140. Sliding the entire balloon catheter 54 distally permits the irregular contours of the distal extremity thereof to pass safely across the valves 106, 110, 112 and into the introducer sheath 70. The loader 140 remains coupled to the introducer 100 during the valve implant procedure, and the loader cap 170 can be re-tightened if necessary to secure the relative positions of the balloon catheter 54 and introducer 100.

The various components of the balloon catheter 54 will now be described with expect to FIG. 5, and the more detailed views of FIGS. 6-15. With reference to the FIGS. 6A and 6B, the balloon inflation connector 152 comprises a main body 186 having a proximal section 188 and a distal section 190. Extending longitudinally through the proximal section 188 is a first bore 192, while extending longitudinally through the distal section 190 is a second bore 194 which communicates with the first bore 192. The first bore 192 has a non-circular cross-sectional configuration for reasons which will be discussed in more detail below. Disposed on the distal end of the distal section 190 is a distal connector nut 196, while disposed on the proximal end of the proximal section 188 is an inflation cap 198 that retains an inflation seal 199 within the inflation connector 152. The second bore 194 widens at its distal end into an enlarged opening that receives a connector nipple 200 also attached within the deflection handle 154.

The balloon catheter 54 of the present invention desirably incorporates relatively sliding concentric inner and outer balloon inflation tubes that attach to opposite ends of the balloon 52. Without going into great detail, the concentric tubes permit the balloon 52 to be shortened or lengthened depending on the relative movement therebetween. This provides the ability to axially extend the balloon 52 after it has been deflated so that its radial profile is reduced and it may be easily removed from the surrounding structures, anatomical or otherwise. Inflation fluid, preferably saline, passes in a tubular space provided between the concentric balloons. In the present invention, the balloon 52 expands the prosthetic heart valve 52 to implant it in the annulus, after which the balloon is deflated and axially elongated before being removed from within the valve. A detailed discussion of the structure and function of this concentric tube configuration may be found in U.S. Pat. No. 5,968,068, the disclosure of which is expressly incorporated by reference herein.

An inner balloon inflation tube 210 is seen at its proximal end extending into the inner tube handle 150 in FIG. 6B, and also in the enlarged view of FIG. 7. The tube 210 fixes concentrically within a tube segment 212 (seen isolated in FIG. 8), a proximal end of which, in turn, is fixed within a bore of the tube handle 150. An anti-rotation block 214 fixed on the distal end of the tube segment 212 axially slides within the first bore 192 of the inflation connector body 186. The first bore 192 and anti-rotation block 214 are non-circular in radial cross-section to prevent relative rotation therebetween. Preferably, these elements are square. This also prevents rotation between the inner tube 210 and the inflation connector 152.

The proximal end of the outer balloon inflation tube 156 is seen in FIGS. 6B and 7 extending into the deflection handle 154 to be fixedly received within the connector nipple 200. As seen in isolation in FIG. 9, the outer balloon inflation tube 156 has a larger cross-section at the distal end of the deflection handle 154 than it does at its termination in the connector nipple 200. An outer portion of the tube 156 fastens within a connector at the distal end of the hollow body 230 of the deflection handle 154, while a smaller diameter fluid-carrying tube 215 extends through the deflection handle to the connector nipple 200. The fluid-carrying tube 215 receives the inner balloon inflation tube 210, while another lumen defined within the outer balloon inflation tube 156 receives a deflection wire, as described below. The connector nipple 200 is fixed (e.g., adhered or similarly secured) with respect to both the inflation connector 152 and deflection handle 154, rendering these two elements essentially contiguous. It can therefore be seen, as in FIG. 6B, that displacement of the inner tube handle 150 with respect to the inflation connector 152 also displaces the inner tube 210 with respect to the outer tube 156.

A Y-port 216 in the distal section 190 of the balloon inflation connector main body 186 leads to a side tube and a stop-cock valve 218. The valve 218 provides a connection point for a source of saline for inflating the balloon 52. The second bore 194 in the main body 186 is open to the first bore 192 which is, in turn, sealed at the inflation cap 198 on the proximal end of the inflation connector 152. Saline thus passes in a distal direction past the connector nipple 200 through a tubular space outside of the inner tube 210 and inside the fluid-carrying tube 215 of the outer tube 156. The concentric space between the tubes 210, 215 provides a pathway for the saline into the distal balloon 152.

Still with reference to FIG. 7, the inner tube handle 150 features a pair of opposed cantilevered clips 220 that serve to temporarily attach the tube handle to the inflation cap 198 on the proximal end of the inflation connector 152. By squeezing the proximal ends of the clips 220 their distal ends open up and the inner tube handle 150 can be displaced in a proximal direction with respect to the inflation cap 198. After a short distance of travel, typically between 1-2 cm, the distal ends of the clips 220 are located over a short flanged nipple 222 on the inflation cap 198 and can be released so that inwardly facing teeth on the clips 220 engaged the flange. This operation displaces the inner balloon inflation tube 210 with respect to the outer balloon inflation tube 156, which in turn causes the opposite axial ends of the balloon 52 to move apart. As mentioned above, this movement facilitates the reduction in profile of the deflated balloon. The interaction between the teeth on the clips 220 and the flanged nipple 222 holds the relative position of the outer and inner tubes 156, 210 such that the balloon 52 remains locked in its extended configuration for ease of removal.

The luer fitting 142 on the proximal end of the inner tube handle 150 provides an entry point for injection of radiographic contrast medium. The luer fitting 142 opens to the lumen of the inner balloon inflation tube 210 which continues to the distal end of the balloon catheter 54 where an egress port is provided. Contrast medium is useful to check for paravalvular leaks after the prosthetic valve is implanted.

Figure 11:
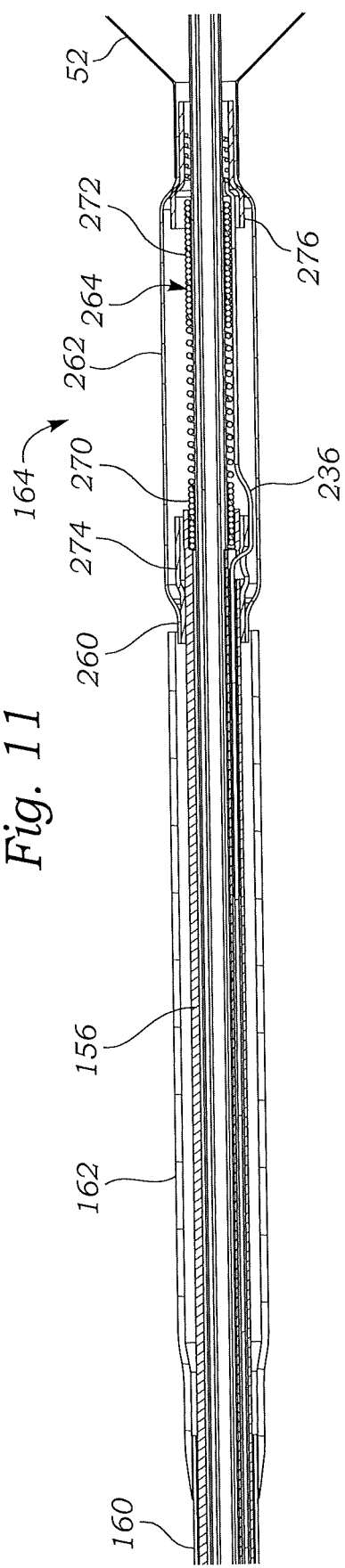
FIG. 11 is an enlarged sectional view of a distal deflecting segment of the balloon catheter as seen in FIG. 6B.

With reference both to FIGS. 6B and 7, the deflection handle 154 includes a generally hollow body 230 having an axial slot on one side that receives a slider 232, seen in FIG. 6A. The hollow body 230 defines a series of partial external circumferential ribs 234 opposite the slider 232 to facilitate gripping by the user. Although it is not readily apparent from the cross-sectional view of FIG. 7, the slider 232 attaches within the handle body 230 to a deflection wire 236 that passes into one of the lumens provided within the larger portion of the outer balloon inflation tube 156. The enlarged view of FIG. 11 illustrates a distal end of the outer tube 156 and shows the deflection wire 236 extending therefrom. Specifics of the attachment of the deflection wire 236 to the distal end of the balloon catheter 54 will be given below. Suffice it to say that axial movement of the slider 232 translates into axial movement of the deflection wire 236.

Figure 10:
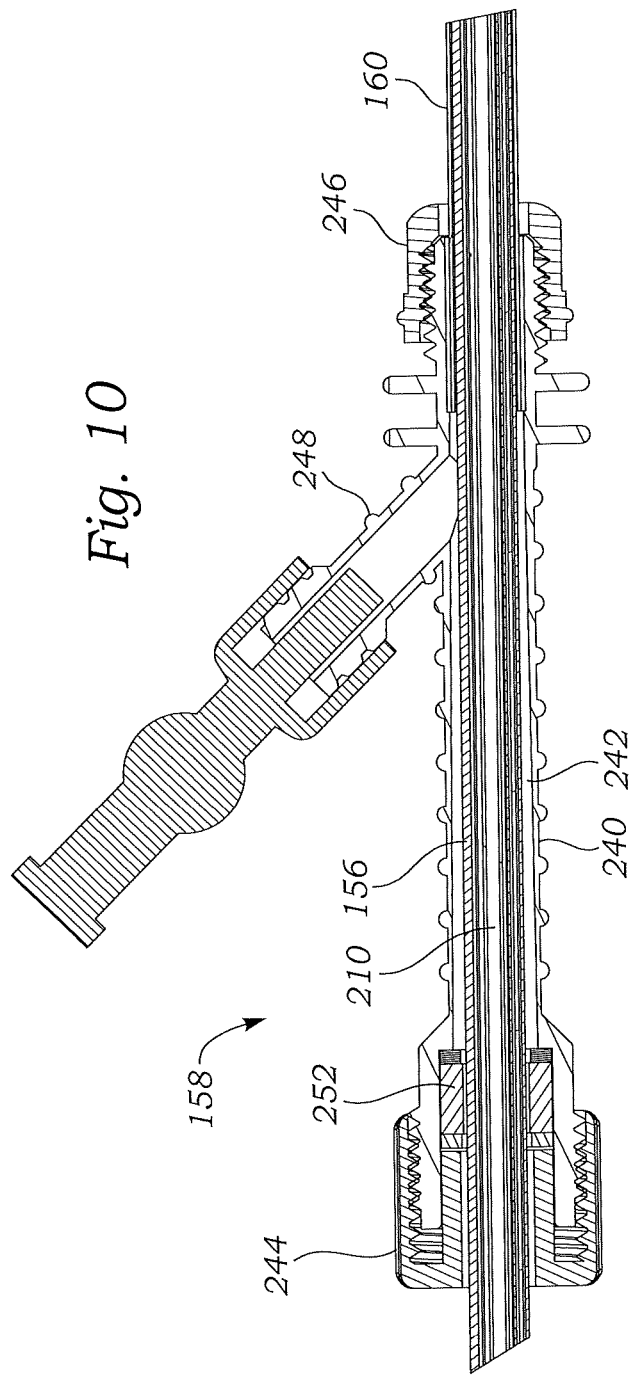
FIG. 10 is an enlarged sectional view of a pusher handle that forms part of the balloon catheter as seen in FIG. 6B.

With reference to FIGS. 6A-6B and 10, the pusher handle 158 comprises a tubular body 240 having a longitudinally extending lumen 242 that slidingly receives the outer tube 156 therethrough. A pair of connector nuts 244, 246 couple to respective proximal and distal ends of the body 240, and in particular mate with external threads provided thereon. A tubular side arm 248 extends angularly from the body 240 and communicates with the lumen 242 therein. The proximal end of the pusher body 160 desirably bonds within the distal end of the body 240, and a lumen defined within the pusher body fluidly communicates with the lumen 242 of the pusher handle body 240. Since the side arm 248 opens into the lumen 242, which surrounds the outer balloon inflation tube 156, fluid introduced through the side arm enters the concentric space between the outer tube 156 and the pusher body 160. The side arm 248 provides a multi-function port for introduction of angiography fluid, heparin, or other such therapeutic substances. The proximal connector nut 244 axially compresses a sealing member 252 to both secure the pusher handle 158 to the outer balloon inflation tube 156, and provide a fluid seal therebetween.

Reference now to FIG. 11, the pusher body 160 attaches on its distal end to a flared pusher sleeve 162. Although shown separated, the pusher sleeve 162 surrounds the deflecting segment 164 and a proximal portion of the balloon 52 during passage through the introducer sheath 70. The deflecting segment 164 generally comprises an outer flexible cover 262 surrounding an inner coil spring 264. The pusher body 160 and pusher sleeve 162 facilitate advancement of the deflecting segment 164 and attached balloon 52 having the valve 50 crimped thereon through the introducer sheath 70. Proximal retraction of the pusher body 160 relative to the outer balloon inflation tube 156 frees the deflecting segment 164 and the balloon 52. As seen best in FIG. 5, the pusher handle 158 may slide proximally over the balloon inflation tube 156 by loosening the proximal connector nut 244, thus pulling the pusher body 160 back with respect to the tube 156.

As mentioned above, the deflection handle 154 supports the slider 232 (FIG. 6A) which is connected to the deflection wire 236, seen extending through the deflecting segment 164 in FIG. 11. In this regard, the deflection wire 236 extends from the deflection handle 154 along one of the lumens in the outer balloon inflation tube 156. The tube 156 terminates just within the flexible cover 262 of the deflecting segment 164, and more particularly is fastened within a rigid proximal tube segment 274 to which the flexible cover 262 also attaches at 260, such as with adhesives. The coil spring 264 desirably includes tightly wound sections 270, 272 at both ends, a proximal one of which is secured within the distal end of the tube 156. The deflection wire 236 exits the outer tube 156 and passes around the outside of the coil spring 264, finally fastening to a distal tube segment 276 of the deflecting segment 164. The tube segment 276 provides a rigid anchor for the flexible cover 262, coil spring 264, and the proximal end of the balloon 52.

Tension in the deflection wire 236 pulls on one side of the distal tube segment 276 which causes the distal end of the deflecting segment 164 to bend in that direction. Of course by rotating the entire balloon catheter 54 about its axis the deflecting segment 164 may be steered in any direction. The coil spring 264 provides both flexibility and resiliency such that release of tension on the deflection wire 236 permits the deflecting segment 164 to return to a straight orientation. Because the balloon 52 attaches to the distal end of the deflecting segment 164, the prosthetic heart valve 50 crimped thereon may be oriented precisely within the native annulus.

With reference again to FIGS. 6A and 6B and 12, the balloon 52 includes a first cone portion 288, a main cylindrical portion 290, and a second cone portion 292. The prosthetic heart valve 50 desirably crimps around the main cylindrical portion 290, such as shown in phantom in FIG. 12. The balloon 52 can be formed of nylon, and is rated at a burst pressure of 6-8 atm. In preferred embodiments, the expanded diameter of the balloon ranges from about 20 to 28 mm, the particular size depending on the size of the heart valve 50 being implanted.

The inner balloon inflation tube 210 passes through the balloon 52 and terminates at a distal end that is capped by the aforementioned soft tip 144, best seen in FIG. 13. The soft tip 144 facilitates introduction of the balloon catheter 54 and reduces trauma to surrounding tissue. This is particularly important in the preferred procedure of the present invention where the catheter enters the apex of the left ventricle and travels through the aortic valve into the ascending aorta. As was seen in FIG. 3D, the distal tip of the catheter may extend far enough to enter the aortic arch, and the soft tip 144 thus prevents rupture or other abrasion to the surrounding vascular tissue. FIG. 13 also illustrates the open distal end of the inner tube 210 and soft tip 144 through which radiographic contrast medium may be injected to test valve sufficiency after implant.

FIG. 14 is an elevational view of the distal end of the balloon catheter 54 showing the balloon 52 deflated and its proximal end encompassed by the pusher sleeve 162. This view also shows a series of inflation holes 298 provided in the inner tube 210 through which saline passes to inflate the balloon 52.

FIG. 15 shows the distal end of the balloon catheter 54 as it is delivered in its packaging. Specifically, a protective sheath 300 is provided surrounding the balloon 52 which is removed in the operating room prior to the implantation procedure.

In use, the present invention provides a novel and effective way for implanting a prosthetic heart valve 50 in the aortic annulus. The steps of the procedure have been described above with respect to FIGS. 1-3, at least as far as the final implantation steps. A description of the advantageous use of the exemplary balloon catheter 54 in performing the entire procedure will now be provided.

First, as mentioned above, the physician determines the size of the patient's annulus. This can be done physically by creating the incision 20 and puncture 32 in the left ventricular apex, and inserting a sizing tool into the aortic annulus. However, the puncture 32 may not be large enough to pass a conventional sizer, and an alternative technique such as echocardiography or other such imaging system may be utilized.

Next, the balloon catheter 54, introducer 100, loader 140, and prosthetic heart valve 50 are selected, and prepared for use by removing them from any packaging and rinsing or sterilizing as needed. A pre-dilation step as described above with respect to FIGS. 2A-2B may be performed to enlarge or crack existing calcification in the aortic annulus.

The process of crimping the prosthetic heart valve 50 over the balloon 52 may be accomplished in a number of ways, and there are suitable devices on the market for crimping balloon-expanding stents over balloons. In a preferred embodiment, a device having a compressing mechanism that works like the aperture iris of a camera is utilized. In such a device, multiple continuous segments around the periphery of the prosthetic heart valve 50 close separately but in concert so that uniform inward pressure is exerted on the heart valve. The devices typically operate manually.

Subsequently, the aforementioned pusher body 160 and flared sleeve 162 are advanced distally over the proximal end of the balloon 52, such as seen in FIG. 14. The pusher handle 158 is secured in this position by screwing tight the connector nut 244. The loader 140 is then secured over the distal end of the balloon catheter 54, including the assembly of the deflecting segment 164, balloon 52 and prosthetic valve 50. The loader 140 fastens in this position through engagement of the loader cap 170 with the proximal threads 172 of the loader body.

At this point, or at the same time as balloon catheter preparation, the introducer 100 is positioned within the left ventricle as seen in FIG. 3A. Again, the purse-string sutures 44 maintain a fluid tight seal around the introducer sheath 70. During the entire procedure the heart may continue beating. The physician inserts the distal nose 174 of the loader 140 into the proximal opening of the introducer housing 102 and bottoms the loader out such that the cantilevered fingers 176 engage the flanged nipple 105 of the introducer. At this point, the balloon catheter 54 is ready for introduction in the body.

Loosening the loader cap 170 permits distal advancement of the balloon catheter 54 with respect to the loader 140 and introducer 100. The physician then retracts the pusher sleeve 162 from the deflecting segment 164 and the proximal portion of the balloon 52 by loosening the connector nut 244 (FIG. 10) and pulling back the pusher handle 158 over the outer balloon inflation tube 156. The physician advances the catheter 54 until it reaches the position shown in FIG. 3C, which also involves retraction of the introducer sheath 70. The entire operation is visualized using radiographic markers and fluoroscopy, and the precise positioning of the balloon 52 and prosthetic valve 50 mounted thereon is accomplished by axial movement and rotation of the catheter 54 coupled with angular changes of the deflecting segment 164. Specifically, as the prosthetic valve 54 advances it is aligned as much as possible along the flow axis of the native aortic valve AV by gross movement of the catheter 54 and slight changes in its angular orientation by tensioning the deflecting wire 236 with the slider 232 (FIG. 6A).

Ultimately, the valve 50 is positioned correctly as in FIG. 3C taking care that the valve 50 is not liable to block either of the coronary ostia 80 when expanded. Saline is then injected through the stopcock 218 (FIG. 6B) which passes through the Y-port 216 and into the tubular space between the outer and inner balloon inflation tubes 156, 210. Saline continues distally through fluid passages in the balloon catheter 54 and fills the balloon 52. The balloon 52 is of a type that has a maximum expanded diameter which has previously been selected to properly expand the prosthetic heart valve 52 to its optimum diameter in contact with the surrounding aortic valve AV, and calcified leaflets if they remain in place. The step is illustrated in FIG. 3D.

Subsequently, saline pressure is reduced within the balloon 52 permitting it to deflate. The deflation may be assisted by axially extending the opposite ends of the balloon 52 by moving the inner tube handle 150 distally toward the inflation handle 152 (see FIG. 6B). Radiographic contrast medium may be injected from the proximal lure 142 of the balloon catheter 54 to egress through the distal soft tip 144 and test the efficacy of the just-implanted prosthetic valve 50. If the valve is properly functioning, the balloon catheter 54 is withdrawn into the introducer sheath 70, which is removed from the puncture 32. The purse-string sutures 44 are closed up to seal the puncture 32.

Once again, the delivery system described herein is particularly well-suited for an antegrade, transapical approach, partly because of its relatively short length. With reference to FIG. 4A, the entire length of the introducer 100 is approximately 13 inches (33 cm), while the length of the sheath 70 that may extend within the body is about 8 inches. The portion of the balloon catheter 54 that extends into the introducer 100 (that is, the portion of the balloon catheter from the distal soft tip 144 to approximately the deflection handle 154) is no more than about 24 inches (61 cm), which permits about 11 inches (28 cm) of the balloon catheter to extend beyond the introducer distal tip 72 (see FIG. 4). It should be noted that the relatively short length of the delivery system is unsuited for a longer, more circuitous approach through the peripheral vasculature, such as shown in co-pending U.S. Pat. No. 7,780,723. Also, the steering mechanism is provided on the balloon catheter 54 itself, rather than on a secondary catheter used for guiding the balloon catheter, as is done in U.S. Pat. No. 7,780,723. The short length of the balloon catheter and the ability to directly manipulate it greatly enhances successful positioning of the prosthetic heart in the aortic annulus.

While the invention has been described in its preferred embodiments, it is to be understood that the words which have been used are words of description and not of limitation. Therefore, changes may be made within the appended claims without departing from the true scope of the invention.

What is claimed is:

1. A minimally-invasive prosthetic heart valve delivery system, comprising:
   an introducer sheath having a lumen therethrough of no greater than 24 French;
   a balloon catheter having a balloon on a distal end, the balloon catheter further including a steering mechanism for deflecting the distal end;
   a balloon-expandable prosthetic heart valve crimped over the balloon,
   wherein the outer dimension of the balloon catheter having the prosthetic heart valve thereon is small enough to pass through the introducer sheath lumen;
   the steering mechanism including a deflecting segment on the balloon catheter located just proximal to the balloon; and
   a deflection wire attached to a distal end of the deflecting segment and extending through the balloon catheter to a proximal deflection handle, and wherein the deflection handle includes a hollow body on which is mounted an actuator connected to pull the deflection wire.

2. The system of claim 1, further including:
   a pusher having a distal sleeve sized to encompass the deflecting segment and a proximal end of the balloon, the pusher being longitudinally movable with respect to the deflecting segment.

3. The system of claim 1, wherein the balloon catheter further includes:
   inner and outer balloon inflation tubes attached to opposite ends of the balloon and arrange to concentrically slide with respect one another to alternately elongate and shorten the balloon;
   an inner tube handle for displacing the inner balloon inflation tube;
   a balloon inflation connector through which the inner balloon inflation tube passes and to which a proximal end of the outer balloon inflation tube attaches; and
   a side port opening to a space defined within the balloon inflation connector, the side port adapted for introducing an inflation fluid into the space and into a tubular space between the inner and outer balloon inflation tubes for inflating the balloon.

4. The system of claim 3, further including:
   wherein the deflection handle is attached just distal to the balloon inflation connector and the outer balloon inflation tube passes through the deflection handle,
   the outer balloon inflation tube including a first lumen for passage of the inner balloon inflation tube, and a second lumen; and
   the deflection wire passes through the second lumen of the outer balloon inflation tube to a distal end of the balloon catheter.

5. The system of claim 1, wherein the balloon catheter has a working length sized to fit into the introducer of no more than about 24 inches (61 cm).

6. The system of claim 5, wherein the introducer has a total length of no more than about 13 inches (33 cm).

7. The system of claim 1, wherein the deflecting segment comprises a coil spring.

8. The system of claim 7, wherein the coil spring has tightly wound sections at both ends and the deflection wire extends around the outside of the coil spring and attaches distally thereto, proximal of the balloon.

9. The system of claim 8, wherein the deflection wire fastens to a distal tube segment of the deflecting segment which provides a rigid anchor for the coil spring and the proximal end of the balloon.

10. The system of claim 1, wherein the hollow body has an axial slot on one side, and the actuator comprises a slider received in the axial slot and connected to pull the deflection wire.

11. The system of claim 1, further including a loader between the introducer sheath and the balloon catheter, the loader having a tube-shaped body with a distal nose that passes into a proximal housing of the introducer sheath and opens a series of valves that provide an effective fluid seal against egress of blood through the introducer sheath in the absence or presence of different sized medical implements.

12. The system of claim 11, wherein the loader includes a pair of attached cantilevered fingers extending parallel thereto with internally facing snap ridges for securing the loader to the introducer housing.

13. The system of claim 11, wherein the loader includes an annular loader seal, the loader further including a loader cap having threads that mate with threads on a main portion of the loader, wherein engagement of the threads axially compresses the loader seal to provide a fluid tight fit and lock the loader axially with respect to the balloon catheter.

14. A minimally-invasive prosthetic heart valve delivery system, comprising:
   an introducer sheath having a lumen therethrough of no greater than 24 French;
   a balloon catheter having a balloon on a distal end, the balloon catheter further including a steering mechanism for deflecting the distal end;
   a balloon-expandable prosthetic heart valve crimped over the balloon,
   wherein the outer dimension of the balloon catheter having the prosthetic heart valve thereon is small enough to pass through the introducer sheath lumen;
   the steering mechanism including a deflecting segment on the balloon catheter located just proximal to the balloon; and
   a loader between the introducer sheath and the balloon catheter, the loader having a tube-shaped body with a distal nose that passes into a proximal housing of the introducer sheath and opens a series of valves that provide an effective fluid seal against egress of blood through the introducer sheath in the absence or presence of different sized medical implements.

15. The system of claim 14, wherein the loader includes a pair of attached cantilevered fingers extending parallel thereto with internally facing snap ridges for securing the loader to the introducer housing.

16. The system of claim 14, wherein the loader includes an annular loader seal, the loader further including a loader cap having threads that mate with threads on a main portion of the loader, wherein engagement of the threads axially compresses the loader seal to provide a fluid tight fit and lock the loader axially with respect to the balloon catheter.

17. The system of claim 14, further including:
   a deflection wire attached to a distal end of the deflecting segment and extending through the balloon catheter to a proximal deflection handle, and wherein the deflection handle includes a hollow body on which is mounted an actuator connected to pull the deflection wire.

18. The system of claim 14, further including:
   a pusher having a distal sleeve sized to encompass the deflecting segment and a proximal end of the balloon, the pusher being longitudinally movable with respect to the deflecting segment.

19. The system of claim 14, wherein the balloon catheter further includes:
   inner and outer balloon inflation tubes attached to opposite ends of the balloon and arrange to concentrically slide with respect one another to alternately elongate and shorten the balloon;
   an inner tube handle for displacing the inner balloon inflation tube;
   a balloon inflation connector through which the inner balloon inflation tube passes and to which a proximal end of the outer balloon inflation tube attaches; and
   a side port opening to a space defined within the balloon inflation connector, the side port adapted for introducing an inflation fluid into the space and into a tubular space between the inner and outer balloon inflation tubes for inflating the balloon.

20. The system of claim 14, wherein the introducer has a total length of no more than about 13 inches (33 cm).

21. The system of claim 20, wherein the balloon catheter has a working length sized to fit into the introducer of no more than about 24 inches (61 cm).

* * * * *